(12) United States Patent
Lawson et al.

(10) Patent No.: US 7,618,983 B2
(45) Date of Patent: Nov. 17, 2009

(54) BICYCLIC TRIAZOLE α4 INTEGRIN INHIBITORS

(75) Inventors: Edward Lawson, Pipersville, PA (US); Bruce Maryanoff, New Hope, PA (US)

(73) Assignee: Janssen Pharmaceutica, N.V. (BE)

( * ) Notice: Subject to any disclaimer, the term of this patent is extended or adjusted under 35 U.S.C. 154(b) by 491 days.

(21) Appl. No.: 11/269,369

(22) Filed: Nov. 8, 2005

(65) Prior Publication Data

US 2006/0128748 A1 Jun. 15, 2006

Related U.S. Application Data

(60) Provisional application No. 60/626,806, filed on Nov. 10, 2004.

(51) Int. Cl.
*A61K 31/4745* (2006.01)
*A61K 31/4196* (2006.01)
*C07D 487/02* (2006.01)
(52) U.S. Cl. .................. 514/303; 514/383; 546/117; 548/264.2
(58) Field of Classification Search .................. None
See application file for complete search history.

(56) References Cited

U.S. PATENT DOCUMENTS 6,303,625 B1 * 10/2001 Hoekstra et al. ............ 514/303

FOREIGN PATENT DOCUMENTS

| EP | 0741133 B1 | 4/1996 |
|---|---|---|
| WO | WO 98/53814 A1 | 12/1998 |
| WO | WO 00/43354 A2 | 7/2000 |
| WO | WO 00/43354 A3 | 7/2000 |
| WO | WO 00/51974 A1 | 9/2000 |
| WO | WO 0144230 A1 | 6/2001 |

OTHER PUBLICATIONS

Wagner et al, "Identification and Characterization of the T Lymphocyte Adhesion Receptor for an Alternative Cell Attachment Domain (CS-1) in Plasma Fibronectin," The Journal of Cell Biology, 1989, pp. 1321-1330, vol. 109, The Rockefeller University Press.
Bayless et al, "Osteopontin is a ligand for the α4β1 integrin," Journal of Cell Science, 1998, pp. 1165-1174, The Company of Biologists Limited, Great Britain.
Chuluyan et al, "α4-Integrin-dependent emigration of monocytes," Springer Semin Immunopathol, 1995, pp. 391-404, vol. 16, Canada.
Adams et al "Section IV. Immunology, Endocrinology and Metabolic Diseases," Chapter 18, Inhibitors of Integrin Alpha 4 Beta 1(vla-4), Annual Reports in Medicinal Chemistry, 1999, pp. 179-188, vol. 34, Academic Press.
Simmons et al, "Vascular Cell Adhesion Molecule-1 Expressed by Bone Marrow Stromal Cells Mediates the Binding of Hematopoietic Progenitor Cells," Blood, 1992, pp. 388-395, vol. 80, No. 2.
Shroff et al, "Novel Modified Tripeptide Inhibitors of α4β7 Mediated Lymphoid Cell Adhesion to MAdCAM-1," Bioorganic & Medicinal Chemistry Letters, 1998, pp. 1601-1606, No. 8, Elsevier Science Ltd.

Yoshikawa et al, "Costimulation of Fibronectin Receptor Promotes FcγR-Mediated Rescue of IL-3-Dependent Bone Marrow-Derived Cells from Apoptosis[1]," J. Immunology, 1996, pp. 1832-1840, vol. 156, The American Association of Immunologists.
Laberge et al, "Role of VLA-4 and LFA-1 in Allergen-Induced Airway Hyperresponsiveness and Lung Inflammation in the Rat," Am J. Respir. Crit. Care Med., 1995, pp. 822-829, vol. 151.
Lin et al, "Selective, Tight-Binding Inhibitors of Integrin α4β1 that Inhibit Allergic Airway Responses," J. Med Chem., 1999, pp. 920-934, vol. 42, American Chemical Society.
Molossi et al, "Blockage of Very Late Antigen-4 Integrin Binding to Fibronectin with Connecting Segment-1 Peptide Reduces Accelerated Coronary Arteriopathy in Rabbit Cardiac Allografts," J. Clin Invest., 1995, pp. 2601-2610, vol. 95, The American Society for Clinical Investigation, Inc.
Kling et al, "Mononuclear Leukocytes Invade Rabbit Arterial Intima During Thickening Formation via CD18- and VLA-4-Dependent Mechanisms and Stimulate Smooth Muscle Migration," Circ Res., 1995, p. 1121-1128, vol. 77, No. 6.
Lumsden et al, "Anti-VLA-4 antibody reduces intimal hyperplasis in the endarterectomized carotid artery in nonhuman primates," J. Vaasc. Surg., 1997, p. 87-93, vol. 26.
Labinaz et al, "Infusion of an antialpha₄ integrin antibody is associated with less neoadventitial formation after balloon injury of porcine coronary arteries," Can J Cardio, 2000, pp. 187-196, vol. 16, No. 2.
O'Brien et al, "Vascular Cell Adhesion Molecule-1 is Expressed in Human Coronary Atherosclerotic Plaques," J. Clin Invest., 1993, pp. 945-951, vol. 92, The American Society for Clinical Investigation, Inc.
Nakashima et al, "Upregulation of VCAM-1 and ICAM-1 at Atherosclerosis-Prone Sites on the Endothelium in the ApoE-Deficient Mouse," Artheriosclerois, Thrombosis, and Vascular Biology, 1998, pp. 842-851, vol. 18.
Iiyama et al, "Patterns of Vascular Cell Adhesion Molecule-1 and Intercellular Adhesion Molecule-1 Expression in Rabbit and Mouse Atherosclerotic Lesions and at Sites Predisposed to Lesion Formation," Circulation Research, 1999, pp. 199-207, vol. 85.
Shih et al, "Blocking Very Late Antigen-4 Integrin Decreases Leukocyte Entry and Fatty Streak Formation in Mice Fed an Atherogenic Diet," Circulation Research, 1999, pp. 345-351, vol. 84.
Huo et al, "Role of Vascular Cell Adhesion Molecule-1 and Fuibronectin Connecting Segment-1 in Monocyte Rolling and Adhesion on Early Atherosclerotic Lesions," Circulation Research, 2000, pp. 153-159, vol. 87.
Hamann et al, "Role of α₄-Integrins in Lymphocyte Homing to Mucosal Tissues In Vivo," Journal of Immunology, 1994, pp. 3282-3293.
Hanninen et al, "Vascular Addressins are Induced on Islet Vessels during Insulitis in Nonobese Diabetic Mice and Are Involved in Lymphoid Cell Binding to Islet Endothelium," The Journal of Clinical Investigation, Inc., 1993, pp. 2590-2515, vol. 92.

(Continued)

*Primary Examiner*—Kamal A Saeed

(57) ABSTRACT

The compounds of the present invention are novel bicyclic triazole amino acid-derivatives useful as α4 integrin receptor antagonists. The invention is further directed to methods for treating integrin mediated disorders including, but not limited to, inflammatory, autoimmune and cell-proliferative disorders, methods for preparing the compounds and methods for preparing the intermediates, derivatives and pharmaceutical compositions thereof.

36 Claims, No Drawings

OTHER PUBLICATIONS

Fong et al, Mucosal Addressin Cell Adhesion Molecule-1 (MAdCAM-1), Immunol. Res., 1997, pp. 299-311, vol. 16.

Yang et al, "Involvement of $\beta_7$ Integrin and Mucosal Addressin Cell Adhesion Molecule-1 (MAdCAM-1) in the Development of Diabetes in Nonobese Diabetic Mice," Diabetes, 1997, pp. 1542-1547, vol. 46.

Gould et al, "Salt selection for basic drugs," International Journal of Pharmaceutics, 1986, pp. 201-217, vol. 33, Elsevier Science Publishers B.V. (Biomedical Division).

Hancock et al, "Characteristics and Significance of the Amorphous State in Pharmaceutical Systems," Journal of Pharmaceutical Sciences, 1997, pp. 1-12, vol. 86, No. 1, publication of the American Pharmaceutical Association and the American Chemical Society.

Powrie et al, "Genetic and spontaneous models of inflammatory bowel disease in rodents: evidence for abnormalities in mucosal immune regulation," Therapeutic Immunology, 1995, pp. 115-123, vol. 2, Blackwell Science Ltd.

Tamraz et al, "Treatment of delayed-type hypersensitivity with inhibitors of the VLA-4 integrin," Spring Semin Immunopathol, 1995, pp. 437-441, vol. 16.

Protective Groups in Organic Chemistry, ed. J.F.W.McOmie, Plenum Press, 1973.

T.W.Greene & P.G.M. Wuts, Protective Groups in Organic Synthesis, John Wiley & Sons, 1991.

Design of Prodrugs, ed. H. Bundgaard, Elsevier, 1985.

Protective Groups in Organic Synthesis, John Wiley & Sons, 1991.

Barbadillo et al, "Anti-integrin immunotherapy in rheumatoid arthritis: protective effect of anti-α4 antibody in adjuvant arthritis," Springer Semin Immunopathol, 1995, pp. 427-436, vol. 16, Springer-Verlag.

* cited by examiner

BICYCLIC TRIAZOLE α4 INTEGRIN INHIBITORS

CROSS-REFERENCE TO RELATED APPLICATIONS

This Application claims priority to U.S. Provisional Patent Application No. 60/626,806, filed Nov. 10, 2004, which is hereby incorporated by reference in its entirety.

FIELD OF THE INVENTION

This invention relates to novel compounds and methods for use in treating integrin mediated disorders. More particularly, this invention relates to novel bicyclic triazole amino acid-derived compounds useful as α4 integrin receptor antagonists, methods for treating integrin mediated disorders including, but not limited to, inflammatory, autoimmune and cell-proliferative disorders. This invention also relates to methods for preparing the instant compounds and methods for preparing intermediates, derivatives and pharmaceutical compositions thereof.

BACKGROUND OF THE INVENTION

Integrin receptors are transmembrane, non-covalently linked heterodimers consisting of one α-chain and one β-chain. In addition to performing a structural adhesive function, integrin receptors transmit extracellular signals across the plasma membrane. The integrin receptor $\alpha_4\beta_1$ (also referred to as VLA-4) mediates cell adhesion by binding with either of two protein ligands: vascular cell adhesion molecule-1 (VCAM-1) (Osborn, L.; et al., *Cell*, 1989, 59, 1203), or the alternatively-spliced fibronectin variant containing the type III connecting segment (CS-1) (Wayner, E. A.; et al., *Cell Biol.*, 1989, 109, 1321). In contrast to the prototypical integrin receptors α5β1, GPIIb/IIIa and $\alpha_v\beta_3$ that recognize the Arg-Gly-Asp (RGD) tripeptide sequence in their respective ligands, $\alpha_4\beta_1$ binds to other primary protein sequences. The $\alpha_4\beta_1$ integrin receptor recognizes Gln-Ile-Asp-Ser (QIDS) in VCAM-1 and Ile-Leu-Asp-Val (ILDV) in fibronectin. Although these sequences share a conserved Asp residue with RGD, they are otherwise unrelated. Additionally, recent studies have found that α4β1 binds the matrix ligand osteopontin (Bayless, K. J.; et al., *J. Cell Sci.*, 1998, 111, 1165). The osteopontin ligand interaction with the $\alpha_4\beta_1$ receptor may be very important as osteopontin is strongly up-regulated in inflammatory settings, including the inflamed lung.

The $\alpha_4\beta_1$ integrin receptor is expressed at high levels on mast cells, mononuclear leukocytes, eosinophils, macrophages, and basophils (Adams, S. P.; et al., *Ann. Rep. Med. Chem.*, 1999, 34, 179). The binding of $\alpha_4\beta_1$ to cytokine-induced VCAM-1 on high-endothelial venules at sites of inflammation results in leukocyte/endothelium adhesion followed by extravasation into the inflamed tissue (Chuluyan, H. E.; et al., *Springer Semin. Immunopathol.*, 1995, 16, 391). The role of mast cells and eosinophils in lung inflammation is well established. Induction of VCAM-1 expression on airway endothelial cells seems to play a central role in lung inflammation. The α4β1 receptor interaction with VCAM-1 also exerts an important effect in stem cell adhesion to bone marrow stromal cells (Simmons, P. J.; et al., *Blood*, 1992, 80, 388).

The $\alpha_4\beta_7$ integrin is expressed at high levels on lymphocytes and T cells. The trafficking of lymphocytes from the vasculature to normal mucosa and lymphoid tissues is mediated by adhesion of mucosal addressing cell adhesion molecule-1 (MAdCAM-1) with the integrin receptor $\alpha_4\beta_7$. In an inflammatory setting, MAdCAM-1, an immunoglobulin superfamily adhesion molecule, specifically binds α4β7-expressing lymphocytes and participates in the homing of these cells to the mucosal endothelium. Cloning studies of human MAdCAM-1 have shown that the Leu-Asp-Thr-Ser-Leu (LDTSL) sequence of the CD loop is conserved. In fact, LDT-based peptides bind to $\alpha_4\beta_7$ in a MAdCAM-1/RPMI-8866 cell adhesion assay with $IC_{50}$ values in the 1-10 uM range (Shroff, H. N.; et al., *Bioorg. Med. Chem. Lett.*, 1998, 8, 1601).

The extensive biology mediated by integrins in general and compelling data for the pathophysiological role of the leukocyte cell adhesion receptor α4β1 have spurred interest in the study of α4β1 antagonists in vivo. Cellular adhesion and migration mediated through the β1 integrins are critical components of cellular recruitment processes. The integrin α4β1 provides a key co-stimulatory signal supporting cell activation leading to growth factor and cytokine production and mediator release. Through recognition of the extracellular matrix, α4β1 increases the survival of activated cells by inhibiting apoptosis (Yoshikawa, H.; et al., *J. Immunol.*, 1996, 156, 1832).

Monoclonal antibodies directed against α4β1 or VCAM-1 have been shown to be effective modulators in animal models of chronic inflammatory diseases such as asthma (Laberge, S.; et al., *Am. J. Respir. Crit. Care Med.*, 1995, 151, 822), rheumatoid arthritis (Barbadillo, C.; et al., *Springer Semin. Immunopathol.*, 1995, 16, 375) and inflammatory bowel disease (Powrie, F.; et al., *Ther. Immunol.*, 1995, 2, 115). The initial research in the low molecular weight α4β1 antagonist arena has focused on simple linear analogues of the prototype Leu-Asp-Val sequence. Phenylacetyl-Leu-Asp-Phe-D-Pro-$NH_2$ (having an α4β1 $IC_{50}$ value of 2 uM) exhibited efficacy similar to the α4 antibody PS/2 in a mouse model of oxazolone-induced contact hypersensitivity when administered at 6 mg/kg, sc (Tamraz, S.; et al., *Springer Semin. Immunopathol.* 1995, 16, 437). This tetrapeptide was also effective in a hyperlipidemic rabbit heterotopic heart allograft model (Molossi, S.; et al., *J. Clin. Invest.* 1995, 95, 2601).

Animal models of asthma have shown that the peptide antagonist BIO-1211 inhibits eosinophilia and airway hyper-responsiveness (Lin, K-C.; et al., *J. Med. Chem.* 1999, 42, 920). Pre-treatment of allergic sheep with a 3 mg nebulized dose of BIO-1211 (having an α4β1 $IC_{50}$ value of 1 nM; 1000-fold selective over α4β7) inhibited early and late airway responses following antigen challenge and prevented development of nonspecific airway hyperresponsiveness to carbachol. These results suggest that compounds like BIO-1211 can effect broad pleiotropic activities by acting at α4β1 to achieve pronounced efficacy similar to corticosteroids.

VLA-4 antagonism may also be effective in reducing restenosis following percutaneous coronary interventions. Administration of an anti-α4 antibody attenuated smooth muscle cell migration associated with electrical injury of rabbit carotid arteries (Kling D, Fingerle J, Harlan J M, Lobb, R R and Lang, F, Mononuclear leukocytes invade rabbit arterial intima during thickening formation via CD-18 and VLA-4-dependent mechanisms and stimulate smooth muscle migration, *Circ. Res.*, 1995, 77, 1121-1128) and was shown to reduce neointimal formation in baboon carotid arteries following endarterectomy (Lumsden A B, Chen C, Hughes J D, Kelly A B, Hanson S and Harker L, Anti-VLA-4 antibody reduces intimal hyperplasia in the endarterectomized carotid artery in non-human primates, *J. Vasc. Surg.*, 1997, 26, 87-93). Furthermore, treatment with z anti-α4 antibody was associated with less neoadventitia formation and less lumenal narrowing 14 days after balloon injury of porcine coronary arteries (Labinez M, Hoffert C, pels K, Aggarawal S, Pepinsky R B, Leonw D, Koteliansky V, Lobb, R R and O'Brien E O, Infusion on and anti-alpha4 integrin antibody is associated with less adventitial formation after balloon injury of porcine coronary arteries, *Can. J. Cardiol.*, 2000, 16, 187-196).

The recruitment of leukocytes, particularly monocytes to the vessel wall is a key component in the development of atherosclerotic lesions. VCAM-1 expression has been reported on endothelial cells in atherosclerotic lesions in humans (O'Brien K D, Allen M D, McDonald T O, Chait A, Harlan J M, Fishbein D, McCarty J, Ferguson M, Hudkins K, Benjamin C D, et al., Vascular cell adhesion molecule-1 is expressed in human atherosclerotic plaques: implications for the mode of progression of advanced atherosclerosis, *J. Clin. Invest.*, 1993, 92, 945-951), mice (Nakahima Y, Raines E W, Plump A S, Breslow J L and Ross R, Upregulation of VCAM-1 and ICAM-1 at atherosclerotic-prone sites on the endothelium of ApoE-deficient mouse, *Arterioscler. Thromb. Vasc. Biol.*, 1998, 18, 842-851) and rabbits (Ilyama K, Hajra L, Iiyam M, Li, H, DiChura M, Medoff B D and Cybulsky M I, Patterns of vascular cell adhesion molecule-1 and intercellular adhesion molecule-1 expression in rabbit and mouse atherosclerotic lesion and at sites predisposed to lesion formation, *Circ. Res.*, 1999, 85, 199-207). Furthermore, a synthetic peptidomimetic of the connecting segment-1 (CS-1) which blocks $\alpha_4\beta_1$ on the leukocyte demonstrated reduced leukocyte homing and lipid accumulation in the aortic sinus in both wild type mice and mice with a low density lipoprotein null mutation (LDLR -/-) maintained on a high fat diet (Shih P T, Brennan M-L, Vora D K, Territo M C, Strahl D, Elices M J, Aldons J and Berliner J A, Blocking very late antigen-4 integrin decreases leukocyte entry and fatty streak formation in mice fed an atherogenic diet, *Circ. Res.*, 1999, 84, 345-351). In studies using isolated carotid arteries from ApoE -/- mice (these mice develop spontaneous arterial atherosclerotic lesions with advanced lesions similar to those observed in humans), administration on blocking antibodies to VCAM-1 inhibited the majority of adhesion of monocytes or U937 cells on early atherosclerotic endothelia. In addition, a peptide which inhibits binding of $\alpha 4\beta 1$ to both VCAM-1 and fibronectin was also effective in this model (Huo Y, Hafez-Moghadem A and Ley K, Role of vascular cell adhesion molecule-1 and fibronectin connecting segment-1 in monocyte rolling and adhesion on early atherosclerotic lesions, *Circ. Res.*, 2000, 87, 153-159). These data support the role of $\alpha_4\beta_1$ in regulating leukocyte recruitment in early and advanced atherosclerotic lesions.

Antibodies to MAdCAM-1 or integrin $\alpha 4\beta 7$ inhibit lymphocyte binding to affinity-purified MAdCAM-1 or MAd-CAM-1 transfectants in vitro (Hamann, A.; et al., *J. Immunol.* 1994,152, 3282). The antibodies also block localization of lymphocytes to Peyer's patches. Murine MAdCAM-1 recognizes only $\alpha 4\beta 7$ positive human lymphocyte cells lines and $\alpha 4\beta 7$-high memory T cells. An in vivo role of $\alpha 4\beta 7$ in inflammation has been suggested by increased expression of MAd-CAM-1 on HEV-type vessels in the chronically inflamed pancreas of the non-obese mouse (Hanninen, A. C.; et al., *J. Clin. Invest.* 1993, 92, 2509). In fact, animal models underscore a significant function of $\alpha 4\beta 7$ in both colitis (Fong, S.; et al., *Immunol. Res.* 1997, 16, 299) and lymphocytic inflammation of pancreatic islets or development of diabetes (Yang, X.; et al., *Diabetes* 1997, 46, 1542).

Accordingly, it is an object of the present invention to provide bicyclic triazole compounds that are α4 integrin receptor antagonists. More particularly, it is an object of the present invention to provide bicyclic triazole compounds that are $\alpha_4\beta_1$ and the $\alpha_4\beta_7$ integrin receptor antagonists. It is also an object of the present invention to provide a process for preparing derivatives of bicyclic triazole amino acid compounds, compositions, intermediates and derivatives thereof. It is a further object of the invention to provide methods for the treatment of integrin mediated disorders that are ameliorated by inhibition of the $\alpha_4\beta_1$ and $\alpha_4\beta_7$ integrin receptors including, but not limited to, inflammatory, autoimmune and cell-proliferative disorders.

It is an object of the present invention to provide methods for producing the instant compounds of Formula (I) and pharmaceutical compositions and medicaments thereof.

It is an object of the present invention to provide methods for the use of bicyclic triazole amino acid compounds in the preparation of a medicament for the treatment of an integrin mediated disorder in a subject in need thereof.

SUMMARY OF THE INVENTION

The present invention is directed to compounds of Formula (I)

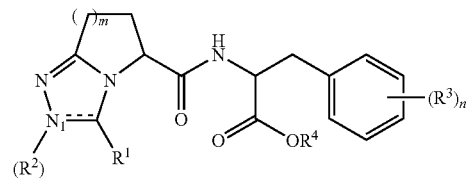

Formula (I)

wherein:
R$^1$ is a substituent selected from the group consisting of hydrogen, C$_{1-4}$alkyl, aryl(C$_{1-8}$)alkyl, heteroaryl(C$_{1-8}$)alkyl, aryl, amino(C$_{1-4}$)alkyl, (C$_{1-4}$)alkylamino(C$_{1-4}$)alkyl, di(C$_{1-4}$)alkylamino(C$_{1-4}$)alkyl, aryl(C$_{1-4}$) alkoxycarbonylamino(C$_{1-4}$)alkyl, heteroaryl(C$_{1-4}$)alkoxycarbonylamino(C$_{1-4}$) alkyl, C$_{1-4}$alkoxycarbonylamino(C$_{1-4}$)alkyl, aryloxycarbonylamino(C$_{1-4}$)alkyl, and oxo; wherein the C$_{1-4}$alkyl substituents of di(C$_{1-4}$)alkylamino(C$_{1-4}$)alkyl are optionally taken together with nitrogen atom to which they are both attached to form a 5 to 8 membered monocyclic ring;
provided that when R$^1$ is a substituent other than oxo, a double bond exists between N$_1$ and the carbon bearing R$^1$; alternatively, when R$^1$ is oxo, then R$^2$ is present;
R$^2$ is selected from the group consisting of hydrogen, C$_{1-4}$alkyl, aryl(C$_{1-4}$)alkyl, and heteroaryl(C$_{1-4}$)alkyl;
m is an integer of 1 or 2;
R$^3$ is a substituent independently selected from the group consisting of C$_{1-8}$alkoxy, heterocyclyl, aryl, heteroaryl, benzo-fused heterocyclyl, —C(=O)NR$^A$R$^B$, —NR$^A$C(=O)aryl, —NR$^A$C(=O)heteroaryl, —NR$^A$C(=O)heterocyclyl, —NR$^A$C(=O)C$_{1-8}$alkyl, —NR$^A$C(=O)C$_{2-8}$alkenyl, —NR$^A$C(=O)C$_{2-8}$alkynyl, —NR$^A$(C=O)C$_{1-8}$alkoxy, —NR$^A$(C=O)C$_{1-8}$alkoxyaryl, —NR$^A$(C=O)C$_{1-8}$alkoxyheteroaryl, —NR$^A$SO$_2$-aryl, —NR$^A$SO$_2$-heteroaryl, —NR$^A$SO$_2$(C$_{1-8}$)alkyl, —NR$^A$C(=O)NR$^A$R$^B$, —NR$^A$C(=O)NR$^A$aryl, —NR$^A$C(=O)NR$^A$heteroaryl, —OC(=O)NR$^A$R$^B$, and halogen;
wherein heterocyclyl and the heterocyclyl-containing substituents of R$^3$, aryl and the aryl-containing substituents of R$^3$, benzo-fused heterocyclyl, and heteroaryl and the heteroaryl-containing substituents of R$^3$ are optionally substituted with one to five substituents independently selected from the group consisting of halogen, $C_{1-8}$alkyl, $C_{2-8}$alkenyl, $C_{2-8}$alkynyl, $C_{1-8}$alkoxy, $C_{1-8}$alkylcarbonyl, $C_{1-8}$alkoxycarbonyl, carboxyl, aryl, heteroaryl, aryloxy, heteroaryloxy, cycloalkyloxy, heterocyclyloxy, benzyloxycarbonyl, arylcarbonyl, heteroarylcarbonyl, arylsulfonyl, amino, $C_{1-8}$alkylamino, $C_{1-8}$dialkylamino, —$CF_3$ and —$OCF_3$; provided that no more than one substituent is selected from the group consisting of aryl, heteroaryl, aryloxy, heteroaryloxy, cycloalkyloxy, heterocyclyloxy, benzyloxycarbonyl, arylcarbonyl, heteroarylcarbonyl, and arylsulfonyl;

and, wherein heterocyclyl of the heterocyclyl-containing substituents of $R^3$ is optionally further substituted with one to three oxo substituents;

$R^A$ is independently selected from the group consisting of hydrogen and $C_{1-8}$alkyl;

$R^B$ is independently selected from the group consisting of hydrogen, $C_{1-8}$alkyl, $C_{2-8}$alkenyl, $C_{2-8}$alkynyl, and $(halo)_{1-3}(C_{1-8})$alkyl; wherein $C_{1-8}$alkyl, $C_{2-8}$alkenyl and $C_{2-8}$alkynyl are optionally substituted with one to three substituents independently selected from the group consisting of heterocyclyl, aryl, and heteroaryl; wherein the heterocyclyl, aryl, and heteroaryl substituents are optionally substituted with benzyloxycarbonyl, arylcarbonyl, or heteroarylcarbonyl, and optionally substituted with one to three substituents independently selected from the group consisting of halogen, $C_{1-8}$alkyl, $C_{2-8}$alkenyl, $C_{2-8}$alkynyl, $C_{1-8}$alkoxy, $C_{1-8}$alkylcarbonyl, $C_{1-8}$alkoxycarbonyl, carboxyl, —$CF_3$ and —$OCF_3$;

n is an integer from 0 to 3;

$R^4$ is a substituent independently selected from the group consisting of hydrogen and $C_{1-4}$alkyl;

and pharmaceutically acceptable enantiomers, diastereomers, racemates, solvates, hydrates, polymorphs, and salts thereof.

An embodiment of the present invention is also directed to a process for preparing the instant bicyclic triazole compounds, compositions, intermediates and derivatives thereof.

Another embodiment of the present invention is directed to pharmaceutical compositions comprising the compounds of the present invention.

Another embodiment of the present invention is directed to the use of bicyclic triazole amino acid compounds of the present invention in the preparation of a medicament for the treatment of an integrin mediated disorder in a subject in need thereof.

The bicyclic triazole derivatives of the present invention are useful α4 integrin receptor antagonists and, more particularly, $α_4β_1$ and $α_4β_7$ integrin receptor antagonists. A further embodiment of the present invention is directed to a method for the treatment of integrin mediated disorders that are ameliorated by inhibition of the $α_4β_1$ and $α_4β_7$ integrin receptor including, but not limited to, inflammatory, autoimmune and cell-proliferative disorders. In an illustration of the invention, the inflammatory, autoimmune and cell-proliferative disorders include, but are not limited to, inflammation and autoimmunity, asthma and bronchoconstriction, restenosis, atherosclerosis, psoriasis, rheumatoid arthritis, inflammatory bowel disease, transplant rejection and multiple sclerosis.

DETAILED DESCRIPTION OF THE INVENTION

Aspects of the present invention include compounds of Formula (I) wherein $R^1$ is independently selected from the group consisting of hydrogen, $C_{1-4}$alkyl, aryl($C_{1-8}$)alkyl, heteroaryl($C_{1-8}$)alkyl, aryl, and oxo; provided that when $R^1$ is a substituent other than oxo, a double bond exists between $N_1$ and the carbon bearing $R^1$; alternatively, when $R^1$ is oxo, then $R^2$ is present.

Aspects of the present invention include compounds of Formula (I) wherein $R^1$ is independently selected from the group consisting of $C_{1-4}$alkyl, aryl($C_{1-4}$)alkyl, heteroaryl($C_{1-4}$)alkyl, phenyl, and oxo, provided that when $R^1$ is a substituent other than oxo, a double bond exists between $N_1$ and the carbon bearing $R^1$; alternatively, when $R^1$ is oxo, then $R^2$ is present.

Aspects of the present invention include compounds of Formula (I) wherein $R^1$ is independently selected from the group consisting of propyl, benzyl, thiophen-3-ylmethyl, indol-3-ylmethyl, phenyl, and oxo; provided that when $R^1$ is a substituent other than oxo, a double bond exists between $N_1$ and the carbon bearing $R^1$; alternatively, when $R^1$ is oxo, then $R^2$ is present.

Aspects of the present invention include compounds of Formula (I) wherein $R^2$ is independently selected from the group consisting of hydrogen, $C_{1-4}$alkyl, and aryl($C_{1-4}$)alkyl.

Aspects of the present invention include compounds of Formula (I) wherein $R^2$ is independently selected from the group consisting of hydrogen and benzyl.

Aspects of the present invention include compounds of Formula (I) wherein m is the integer 1.

Aspects of the present invention include compounds of Formula (I) wherein $R^3$ is a substituent independently selected from the group consisting of $C_{1-6}$alkoxy, —C(=O)$NR^AR^B$, —$NR^AC$(=O)aryl, —$NR^AC$(=O)heteroaryl, —$NR^AC$(=O)heterocyclyl, —$NR^AC$(=O)$C_{1-8}$alkyl, —$NR^ASO_2$-aryl, —$NR^ASO_2$-heteroaryl, —$NR^ASO_2(C_{1-8})$alkyl, —$NR^AC$(=O)$NR^AR^B$, —$NR^AC$(=O)$NR^A$aryl, —$NR^AC$(=O)$NR^A$heteroaryl, —OC(=O)$NR^AR^B$, and halogen; wherein the heterocyclyl portion of —$NR^AC$(=O)heterocyclyl, the aryl portion of the aryl-containing substituents of $R^3$, and the heteroaryl portion of the heteroaryl-containing substituents of $R^3$ are optionally substituted with one to three substituents independently selected from the group consisting of halogen, $C_{1-4}$alkyl, $C_{1-4}$alkoxy, $C_{1-4}$alkylcarbonyl, $C_{1-4}$alkoxycarbonyl, amino, $C_{1-8}$alkylamino, $C_{1-8}$dialkylamino, —$CF_3$ and —$OCF_3$; and, wherein heterocyclyl of —$NR^AC$(=O)heterocyclyl is optionally further substituted with one to two oxo substituents.

Aspects of the present invention include compounds of Formula (I) wherein $R^3$ is a substituent independently selected from the group consisting of $C_{1-3}$alkoxy, —C(=O)$NR^AR^B$, —$NR^AC$(=O)aryl, —$NR^AC$(=O)heteroaryl, —$NR^AC$(=O)$C_{1-4}$alkyl, —$NR^ASO_2$-aryl, —$NR^ASO_2$-heteroaryl, —$NR^ASO_2(C_{1-4})$alkyl, —OC(=O)$NR^AR^B$, and halogen; wherein the aryl portion of the aryl-containing substituents of $R^3$, and the heteroaryl portion of the heteroaryl-containing substituents of $R^3$ are optionally substituted with one to three substituents independently selected from the group consisting of halogen, $C_{1-4}$alkyl, $C_{1-4}$alkoxy, and $C_{1-4}$alkoxycarbonyl.

Aspects of the present invention include compounds of Formula (I) wherein $R^3$ is a substituent independently selected from the group consisting of —$NR^AC$(=O)phenyl, —$NR^AC$(=O)naphthalenyl, —$NR^AC$(=O)pyridin-4-yl, —$NR^AC$(=O)$C_{1-4}$alkyl, and —OC(=O)$NMe_2$; wherein phenyl, naphthalenyl, and pyridin-4-yl are optionally substituted with one to three substituents independently selected from the group consisting of chloro, methyl, methoxy, ethoxy, and methoxycarbonyl.

Aspects of the present invention include compounds of Formula (I) wherein $R^3$ is a substituent independently selected from the group consisting of —NHC(=O)2,6- dichlorophenyl, —NHC(═O)2,6-dimethoxyphenyl, —NHC(═O)naphthalen-1-yl, —NHC(═O)2-ethoxy-naphthalen-1-yl, —NHC(═O)naphthalen-2-yl, and —NHC(═O)3,5-dichloro-pyridin-4-yl.

Aspects of the present invention include compounds of Formula (I) wherein $R^3$ is attached at the 4-position of the phenyl ring of Formula (I) and n is 1.

Aspects of the present invention include compounds of Formula (I) wherein $R^A$ is independently selected from the group consisting of hydrogen and methyl.

Aspects of the present invention include compounds of Formula (I) wherein $R^B$ is independently selected from the group consisting of hydrogen, $C_{1-6}$alkyl, and $(halo)_{1-3}(C_{1-6})$alkyl; wherein $C_{1-6}$alkyl is optionally substituted with one to three substituents independently selected from the group consisting of heterocyclyl, aryl, and heteroaryl; wherein the heterocyclyl, aryl, and heteroaryl substituents are optionally substituted with benzyloxycarbonyl, arylcarbonyl, heteroarylcarbonyl, and optionally further substituted with one to three substituents independently selected from the group consisting of halogen, $C_{1-8}$alkyl, $C_{1-8}$alkoxy, $C_{1-8}$alkylcarbonyl, $C_{1-8}$alkoxycarbonyl, carboxyl, —$CF_3$ and —$OCF_3$.

Aspects of the present invention include compounds of Formula (I) wherein $R^B$ is independently selected from the group consisting of hydrogen and $C_{1-4}$alkyl, wherein $C_{1-4}$alkyl is optionally substituted with one to three substituents independently selected from the group consisting of heterocyclyl, aryl, and heteroaryl.

Aspects of the present invention include compounds of Formula (I) wherein $R^B$ is independently selected from the group consisting of hydrogen and $C_{1-4}$alkyl.

Aspects of the present invention include compounds of Formula (I) wherein n is an integer from 0 to 2.

Aspects of the present invention include compounds of Formula (I) wherein n is an integer of 1.

Aspects of the present invention include compounds of Formula (I) wherein $R^4$ is a substituent independently selected from the group consisting of hydrogen and $C_{1-4}$alkyl.

Aspects of the present invention include compounds of Formula (I) wherein $R^4$ is a substituent independently selected from the group consisting of hydrogen and methyl.

The present invention includes pharmaceutically acceptable enantiomers, diastereomers, racemates, solvates, hydrates, polymorphs, and salts of the compounds described in any one of the embodiments herein.

Aspects of the present invention include compounds of Formula (Ia)

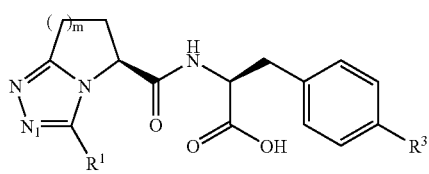

Formula (Ia)

selected from the group consisting of:
a compound of Formula (Ia) wherein $R^1$ is phenyl, m is 2, and $R^3$ is —O(C═O)NMe$_2$;
a compound of Formula (Ia) wherein $R^1$ is —CH$_2$Ph, m is 2, and $R^3$ is —O(C═O)NMe$_2$;
a compound of Formula (Ia) wherein $R^1$ is —CH$_2$Ph, m is 1, and $R^3$ is —O(C═O)NMe$_2$;
a compound of Formula (Ia) wherein $R^1$ is —CH$_2$Ph, m is 1, and $R^3$ is —NH(C═O)2,6-dichlorophenyl;

a compound of Formula (Ia) wherein $R^1$ is —CH$_2$Ph, m is 1, and $R^3$ is —NH(C═O)naphthalen-1-yl;
a compound of Formula (Ia) wherein $R^1$ is —CH$_2$Ph, m is 1, and $R^3$ is —NH(C═O)naphthalen-2-yl;
a compound of Formula (Ia) wherein $R^1$ is —CH$_2$Ph, m is 1, and $R^3$ is —NH(C═O)(2-ethoxy)-naphthalen-1-yl;
a compound of Formula (Ia) wherein $R^1$ is —CH$_2$Ph, m is 1, and $R^3$ is —NH(C═O)fluoren-9-on4-yl;
a compound of Formula (Ia) wherein $R^1$ is —CH$_2$Ph, m is 1, and $R^3$ is —NH(C═O)(3,5-dichloro)-pyridin-4-yl;
a compound of Formula (Ia) wherein $R^1$ is n-propyl, m is 1, and $R^3$ is —NH(C═O)2,6-dichlorophenyl;
a compound of Formula (Ia) wherein $R^1$ is —CH$_2$NH(C═O)OCH$_2$Ph, m is 1, and $R^3$ is —NH(C═O)2,6-dichlorophenyl;
a compound of Formula (Ia) wherein $R^1$ is —CH$_2$-thiophen-3-yl, m is 1, and $R^3$ is —NH(C═O)2,6-dichlorophenyl;
a compound of Formula (Ia) wherein $R^1$ is —CH$_2$Ph, m is 1, and $R^3$ is 2,6-dimethoxy-phenyl;
a compound of Formula (Ia) wherein $R^1$ is —CH$_2$NH$_2$, m is 1, and $R^3$ is —NH(C═O)2,6-dichlorophenyl;
a compound of Formula (Ia) wherein $R^1$ is —CH$_2$-thiophen-3-yl, m is 1, and $R^3$ is 2,6-dimethoxy-phenyl;
a compound of Formula (Ia) wherein $R^1$ is —CH$_2$-indol-3-yl, m is 1, and $R^3$ is 2,6-dimethoxy-phenyl; and
a compound of Formula (Ia) wherein $R^1$ is —CH$_2$Ph, m is 1, and $R^3$ is 5-methoxy-2-methyl-2H-pyridazin-3-on4-yl;
and pharmaceutically acceptable enantiomers, diastereomers, racemates, solvates, hydrates, polymorphs, and salts thereof.

Aspects of the present invention include compounds of Formula (Ib)

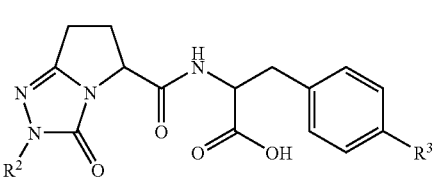

Formula (Ib)

selected from the group consisting of
a compound of Formula (Ib) wherein $R^2$ is H and $R^3$ is —NH(C═O)2,6-dichloro-phenyl;
a compound of Formula (Ib) wherein $R^2$ is —CH$_2$Ph and $R^3$ is —NH(C═O)2,6-dichlorophenyl;
a compound of Formula (Ib) wherein $R^2$ is H and $R^3$ is —NHC(═O)3,5-dichloro-pyridin-4-yl; and
a compound of Formula (Ib) wherein $R^2$ is —CH$_2$Ph and $R^3$ is —NHC(═O)3,5-dichloro-pyridin-4-yl;
and pharmaceutically acceptable enantiomers, diastereomers, racemates, solvates, hydrates, polymorphs, and salts thereof.

Additional embodiments of the present invention include those wherein the substituents selected for one or more of the variables defined herein (i.e. $R^1$, $R^2$, m, $R^3$, n, $R^4$, $R^A$, and $R^B$) are independently selected to be any individual substituent or any subset of substituents selected from the description provided herein.

The compounds of the present invention may also be present in the form of pharmaceutically acceptable salts. For use in medicine, the salts of the compounds of this invention refer to non-toxic "pharmaceutically acceptable salts" (Ref. *International J. Pharm.*, 1986, 33, 201-217; *J. Pharm. Sci.*, 1997 (January), 66, 1, 1). Other salts may, however, be useful in the preparation of compounds according to this invention or of their pharmaceutically acceptable salts. Representative organic or inorganic acids include, but are not limited to, hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or trifluoroacetic acid. Representative organic or inorganic bases include, but are not limited to, basic or cationic salts such as benzathine, chloroprocaine, choline, diethanolamine, ethylenediamine, meglumine, procaine, aluminum, calcium, lithium, magnesium, potassium, sodium and zinc.

The present invention includes within its scope prodrugs of the compounds of this invention. In general, such prodrugs will be functional derivatives of the compounds, which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the subject. Conventional procedures for the selection and preparation of suitable prodrug derivatives are described, for example, in "*Design of Prodrugs*", ed. H. Bundgaard, Elsevier, 1985.

Where the compounds according to this invention have at least one chiral center, they may accordingly exist as enantiomers. Where the compounds possess two or more chiral centers, they may additionally exist as diastereomers. Where the processes for the preparation of the compounds according to the invention give rise to mixtures of stereoisomers, these isomers may be separated by conventional techniques such as preparative chromatography. The compounds may be prepared in racemic form or as individual enantiomers or diasteromers by either stereospecific synthesis or by resolution. The compounds may, for example, be resolved into their component enantiomers or diasteromers by standard techniques, such as the formation of stereoisomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of stereoisomeric esters or amides, followed by chromatographic separation and removal of the chiral auxiliary. Alternatively, the compounds may be resolved using a chiral HPLC column. It is to be understood that all stereoisomers, racemic mixtures, diastereomers and enantiomers thereof are encompassed within the scope of the present invention.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J.F.W. McOmie, Plenum Press, 1973; and T.W. Greene & P.G.M. Wuts, *Protective Groups in Organic Synthesis*, John Wiley & Sons, 1991. The protecting groups may be removed at a convenient subsequent stage using methods known in the art.

Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

As used herein, unless otherwise noted, "alkyl" whether used alone or as part of a substituent group refers to straight and branched carbon chains having 1 to 8 carbon atoms or any number within this range. Therefore, designated numbers of carbon atoms (e.g. $C_{1-8}$) shall refer independently to the number of carbon atoms in an alkyl or cycloalkyl moiety or to the alkyl portion of a larger substituent in which alkyl appears as its prefix root.

As used herein, unless otherwise noted, the term "alkoxy" refers to an —Oalkyl substituent group, wherein alkyl is as defined supra. Similarly, the terms "alkenyl" and "alkynyl" refer to straight and branched carbon chains having 2 to 8 carbon atoms or any number within this range, wherein an alkenyl chain has at least one double bond in the chain and an alkynyl chain has at least one triple bond in the chain. An alkyl and alkoxy chain may be substituted on a carbon atom. In substituent groups with multiple alkyl groups such as $(C_{1-6}alkyl)_2$amino- the $C_{1-6}$alkyl groups of the dialkylamino may be the same or different.

As used herein, unless otherwise noted "oxo" whether used alone or as part of a substituent group refers to an O= to either a carbon or a sulfur atom. For example, phthalimide and saccharin are examples of compounds with oxo substituents.

The term "heterocyclyl" as used herein refers to an optionally substituted, stable, saturated or partially saturated 5 or 7 membered monocyclic ring which consists of carbon atoms and from one to three heteroatoms selected from N, O or S. Examples of heterocyclyl groups include, but are not limited to, pyrrolinyl (including 2H-pyrrole, 2-pyrrolinyl or 3-pyrrolinyl), pyrrolidinyl, dioxolanyl, 2-imidazolinyl, imidazolidinyl, 2-pyrazolinyl, pyrazolidinyl, piperidinyl, dioxanyl, morpholinyl, dithianyl, thiomorpholinyl or piperazinyl. The heterocyclyl group may be attached at any heteroatom or carbon atom that results in the creation of a stable structure.

The term "aryl" refers to an unsaturated, aromatic monocyclic ring of 6 carbon members or to an unsaturated, aromatic polycyclic ring of from 10 to 14 carbon members. Examples of such aryl rings include, and are not limited to, phenyl, naphthalenyl or anthracenyl. Preferred aryl groups for the practice of this invention are phenyl and naphthalenyl.

The term "heteroaryl" as used herein represents a stable five or six membered monocyclic aromatic ring system or a nine or ten membered benzo-fused heteroaromatic ring system which consists of carbon atoms and from one to three heteroatoms selected from N, O or S. The heteroaryl group may be attached at any heteroatom or carbon atom which results in the creation of a stable structure. Examples of heteroaryl groups include, and are not limited to, furyl, thiophenyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyridazinonyl, pyrimidinyl or pyrazinyl; fused heteroaryl groups include indolyl, isoindolyl, indolinyl, benzofuryl, benzothienyl, indazolyl, benzimidazolyl, benzthiazolyl, benzoxazolyl, benzisoxazolyl, benzothiadiazolyl, benzotriazolyl, quinolizinyl, quinolinyl, isoquinolinyl or quinazolinyl. Preferred examples in the practice of this invention include pyridinyl, thiophenyl, indolyl, and pyridazinonyl.

The term "arylalkyl" means an alkyl group substituted with an aryl group (e.g., benzyl, phenethyl). The term "arylalkoxy" indicates an alkoxy group substituted with an aryl group (e.g., benzyloxy, phenethoxy, etc.). Similarly, the term "aryloxy" indicates an oxy group substituted with an aryl group (e.g., phenoxy).

The term "halogen" refers to fluorine, chlorine, bromine and iodine. Substituents that are substituted with multiple halogens are substituted in a manner that provides compounds which are stable. Chlorine is a preferred halogen in the present invention.

Whenever the term "alkyl" or "aryl" or either of their prefix roots appear in a name of a substituent (e.g., aralkyl, alkylamino) it shall be interpreted as including those limitations given above for "alkyl" and "aryl." Designated numbers of carbon atoms (e.g., $C_{1-6}$) shall refer independently to the number of carbon atoms in an alkyl or cycloalkyl moiety or to the alkyl portion of a larger substituent in which alkyl appears as its prefix root. For alkyl and alkoxy substituents, the designated number of carbon atoms includes all of the independent members included in the range specified individually and all the combination of ranges within in the range specified. For example $C_{1-6}$ alkyl includes, but is not limited to, methyl, ethyl, propyl, butyl, pentyl and hexyl individually as well as sub-combinations thereof (e.g. $C_{1-2}$, $C_{1-3}$, $C_{1-4}$, $C_{1-5}$, $C_{2-6}$, $C_{3-6}$, $C_{4-6}$, $C_{5-6}$, $C_{2-5}$, etc.).

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

The bicyclic triazole amino acid compounds of the present invention are useful α4 integrin receptor antagonists and, more particularly, α4β1 and α4β7 integrin receptor antagonists for treating a variety of integrin mediated disorders that are ameliorated by inhibition of the α4β1 and α4β7 integrin receptor including, but not limited to, inflammatory, autoimmune and cell-proliferative disorders.

Illustrative of the invention is a pharmaceutical composition comprising a pharmaceutically acceptable carrier and any of the compounds described above. Also illustrative of the invention is a pharmaceutical composition made by mixing any of the compounds described above and a pharmaceutically acceptable carrier. A further illustration of the invention is a process for making a pharmaceutical composition comprising mixing any of the compounds described above and a pharmaceutically acceptable carrier. The present invention also provides pharmaceutical compositions comprising one or more compounds of this invention in association with a pharmaceutically acceptable carrier.

An example of the invention is a method for the treatment of integrin mediated disorders in a subject in need thereof comprising administering to the subject a therapeutically effective amount of any of the compounds or pharmaceutical compositions described above. Also included in the invention is the use of a compound of Formula (I) for the preparation of a medicament for treating an integrin mediated disorder in a subject in need thereof.

Further exemplifying the invention is the method for the treatment of integrin mediated disorders, wherein the therapeutically effective amount of the compound is from about 0.01 mg/kg/day to about 30 mg/kg/day.

In accordance with the methods of the present invention, the individual components of the pharmaceutical compositions described herein can be administered separately at different times during the course of therapy or concurrently in divided or single combination forms. The instant invention is therefore to be understood as embracing all such regimes of simultaneous or alternating treatment and the term "administering" is to be interpreted accordingly.

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal, or human, that is being sought by a researcher, veterinarian, medical doctor, or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

The utility of the compounds to treat integrin mediated disorders can be determined according to the procedures herein. The present invention therefore provides a method for the treatment of integrin mediated disorders in a subject in need thereof which comprises administering any of the compounds as defined herein in a quantity effective to inhibit the α4β1 and α4β7 integrin receptor including, but not limited to, inflammatory, autoimmune and cell-proliferative disorders. Accordingly, a compound of the present invention may be administered by any conventional route of administration including, but not limited to oral, nasal, pulmonary, sublingual, ocular, transdermal, rectal, vaginal and parenteral (i.e. subcutaneous, intramuscular, intradermal, intravenous etc.).

To prepare the pharmaceutical compositions of this invention, one or more compounds of Formula (I) or salt thereof as the active ingredient, is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

In preparing a pharmaceutical composition of the present invention in liquid dosage form for oral, topical and parenteral administration, any of the usual pharmaceutical media or excipients may be employed. Thus, for liquid dosage forms, such as suspensions (i.e. colloids, emulsions and dispersions) and solutions, suitable carriers and additives include but are not limited to pharmaceutically acceptable wetting agents, dispersants, flocculation agents, thickeners, pH control agents (i.e. buffers), osmotic agents, coloring agents, flavors, fragrances, preservatives (i.e. to control microbial growth, etc.) and a liquid vehicle may be employed. Not all of the components listed above will be required for each liquid dosage form.

In solid oral preparations such as, for example, dry powders for reconstitution or inhalation, granules, capsules, caplets, gelcaps, pills and tablets (each including immediate release, timed release and sustained release formulations), suitable carriers and additives include but are not limited to diluents, granulating agents, lubricants, binders, glidants, disintegrating agents and the like. Because of their ease of administration, tablets and capsules represent the most advantageous oral dosage unit form, in which case solid pharmaceutical carriers are obviously employed. If desired, tablets may be sugar coated, gelatin coated, film coated or enteric coated by standard techniques.

The pharmaceutical compositions herein will contain, per dosage unit, e.g., tablet, capsule, powder, injection, teaspoonful and the like, an amount of the active ingredient necessary to deliver an effective dose as described above. The therapeutically effective amount of the compounds of Formula (I) exemplified in such a method is from about 0.01 mg/kg/day to about 300 mg/kg/day. Particularly, the range is from about 0.5 to about 5.0 mg/kg of body weight per day; and more particularly, from about 1.0 to about 3.0 mg/kg of body weight per day. The compounds may be administered on a regimen of 1 to 4 times per day.

Preferably, for the method of treating integrin mediated disorders described in the present invention using any of the compounds as defined herein, the dosage form will contain a pharmaceutically acceptable carrier containing between about 0.01 mg and 100 mg, more preferably about 5 to 50 mg, of the compound, and may be constituted into any form suitable for the mode of administration selected. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, dry powders for reconstitution or inhalation, granules, lozenges, sterile parenteral solutions or suspensions, metered aerosol or liquid sprays, drops, ampoules, autoinjector devices or suppositories for administration by oral, intranasal, sublingual, intraocular, transdermal, parenteral, rectal, vaginal, dry powder inhaler or other inhalation or insufflation means. Alternatively, the composition may be presented in a form suitable for once-weekly or once-monthly administration; for example, an insoluble salt of the active compound, such as the decanoate salt, may be adapted to provide a depot preparation for intramuscular injection.

For preparing solid pharmaceutical compositions such as tablets, the principal active ingredient is mixed with a pharmaceutical carrier, e.g. conventional tableting ingredients such as diluents, binders, adhesives, disintegrants, lubricants, antiadherents and gildants. Suitable diluents include, but are not limited to, starch (i.e. corn, wheat, or potato starch, which may be hydrolized), lactose (granulated, spray dried or anhydrous), sucrose, sucrose-based diluents (confectioner's sugar; sucrose plus about 7 to 10 weight percent invert sugar; sucrose plus about 3 weight percent modified dextrins; sucrose plus invert sugar, about 4 weight percent invert sugar, about 0.1 to 0.2 weight percent cornstarch and magnesium stearate), dextrose, inositol, mannitol, sorbitol, microcrystalline cellulose (i.e. AVICEL™ microcrystalline cellulose available from FMC Corp.), dicalcium phosphate, calcium sulfate dihydrate, calcium lactate trihydrate and the like. Suitable binders and adhesives include, but are not limited to acacia gum, guar gum, tragacanth gum, sucrose, gelatin, glucose, starch, and cellulosics (i.e. methylcellulose, sodium carboxymethylcellulose, ethylcellulose, hydroxypropylmethylcellulose, hydroxypropylcellulose, and the like), water soluble or dispersible binders (i.e. alginic acid and salts thereof, magnesium aluminum silicate, hydroxyethylcellulose [i.e. TYLOSE™ available from SE TYLOSE GmbH & Co. KG], polyethylene glycol, polysaccharide acids, bentonites, polyvinylpyrrolidone, polymethacrylates and pregelatinized starch) and the like. Suitable disintegrants include, but are not limited to, starches (corn, potato, etc.), sodium starch glycolates, pregelatinized starches, clays (magnesium aluminum silicate), celluloses (such as crosslinked sodium carboxymethylcellulose and microcrystalline cellulose), alginates, pregelatinized starches (i.e. corn starch, etc.), gums (i.e. agar, guar, locust bean, karaya, pectin, and tragacanth gum), cross-linked polyvinylpyrrolidone and the like. Suitable lubricants and antiadherents include, but are not limited to, stearates (magnesium, calcium and sodium), stearic acid, talc waxes, stearowet, boric acid, sodium chloride, DL-leucine, carbowax 4000, carbowax 6000, sodium oleate, sodium benzoate, sodium acetate, sodium lauryl sulfate, magnesium lauryl sulfate and the like. Suitable gildants include, but are not limited to, talc, cornstarch, silica (i.e. CAB-O-SIL™ silica available from Cabot, SYLOID™ silica available from W.R. Grace/Davison, and AEROSIL™ silica available from Degussa) and the like. Sweeteners and flavorants may be added to chewable solid dosage forms to improve the palatability of the oral dosage form. Additionally, colorants and coatings may be added or applied to the solid dosage form for ease of identification of the drug or for aesthetic purposes. These carriers are formulated with the pharmaceutical active to provide an accurate, appropriate dose of the pharmaceutical active with a therapeutic release profile.

Generally these carriers are mixed with the pharmaceutical active to form a solid preformulation composition containing a homogeneous mixture of the pharmaceutical active of the present invention, or a pharmaceutically acceptable salt thereof. Generally the preformulation will be formed by one of three common methods: (a) wet granulation, (b) dry granulation and (c) dry blending. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from about 0.1 mg to about 500 mg of the active ingredient of the present invention. The tablets or pills containing the novel compositions may also be formulated in multilayer tablets or pills to provide a sustained or provide dual-release products. For example, a dual release tablet or pill can comprise an inner dosage and an outer dosage component, the latter being in the form of an envelope over the former. The two components can be separated by an enteric layer, which serves to resist disintegration in the stomach and permits the inner component to pass intact into the duodenum or to be delayed in release. A variety of materials can be used for such enteric layers or coatings, such materials including a number of polymeric materials such as shellac, cellulose acetate (i.e. cellulose acetate phthalate, cellulose acetate trimetilitate), polyvinyl acetate phthalate, hydroxypropyl methylcellulose phthalate, hydroxypropyl methylcellulose acetate succinate, methacrylate and ethylacrylate copolymers, methacrylate and methyl methacrylate copolymers and the like. Sustained release tablets may also be made by film coating or wet granulation using slightly soluble or insoluble substances in solution (which for a wet granulation acts as the binding agents) or low melting solids a molten form (which in a wet granulation may incorporate the active ingredient). These materials include natural and synthetic polymers waxes, hydrogenated oils, fatty acids and alcohols (i.e. beeswax, carnauba wax, cetyl alcohol, cetylstearyl alcohol, and the like), esters of fatty acids metallic soaps, and other acceptable materials that can be used to granulate, coat, entrap or otherwise limit the solubility of an active ingredient to achieve a prolonged or sustained release product.

The liquid forms in which the novel compositions of the present invention may be incorporated for administration orally or by injection may include, but are not limited to aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable suspending agents for aqueous suspensions, include synthetic and natural gums such as, acacia, agar, alginate (i.e. propylene alginate, sodium alginate and the like), guar, karaya, locust bean, pectin, tragacanth, and xanthan gum, cellulosics such as sodium carboxymethylcellulose, methylcellulose, hydroxymethylcellulose, hydroxyethylcellulose, hydroxypropyl cellulose and hydroxypropyl methylcellulose, and combinations thereof, synthetic polymers such as polyvinyl pyrrolidone, carbomer (i.e. carboxypolymethylene), and polyethylene glycol; clays such as bentonite, hectorite, attapulgite or sepiolite; and other pharmaceutically acceptable suspending agents such as lecithin, gelatin or the like. Suitable surfactants include but are not limited to sodium docusate, sodium lauryl sulfate, polysorbate, octoxynol-9, nonoxynol-10, polysorbate 20, polysorbate 40, polysorbate 60, polysorbate 80, polyoxamer 188, polyoxamer 235 and combinations thereof. Suitable deflocculating or dispersing agent include pharmaceutical grade lecithins. Suitable flocculating agent include but are not limited to simple neutral electrolytes (i.e. sodium chloride, potassium, chloride, and the like), highly charged insoluble polymers and polyelectrolyte species, water soluble divalent or trivalent ions (i.e. calcium salts, alums or sulfates, citrates and phosphates (which can be used jointly in formulations as pH buffers and flocculating agents). Suitable preservatives include but are not limited to parabens (i.e. methyl, ethyl, n-propyl and n-butyl), sorbic acid, thimerosal, quaternary ammonium salts, benzyl alcohol, benzoic acid, chlorhexidine gluconate, phenylethanol and the like. There are many liquid vehicles that may be used in liquid pharmaceutical dosage forms, however, the liquid vehicle that is used in a particular dosage form must be compatible with the suspending agent(s). For example, nonpolar liquid vehicles such as fatty esters and oils liquid vehicles are best used with suspending agents such as low HLB (Hydrophile-Lipophile Balance) surfactants, stearalkonium hectorite, water insoluble resins, water insoluble film forming polymers and the like. Conversely, polar liquids such as water, alcohols, polyols and glycols are best used with suspending agents such as higher HLB surfactants, clays silicates, gums, water soluble cellulosics, water soluble polymers and the like. For parenteral administration, sterile suspensions and solutions are desired. Liquid forms useful for parenteral administration include sterile solutions, emulsions and suspensions. Isotonic preparations which generally contain suitable preservatives are employed when intravenous administration is desired.

Furthermore, compounds of the present invention can be administered in an intranasal dosage form via topical use of suitable intranasal vehicles or via transdermal skin patches, the composition of which are well known to those of ordinary skill in that art. To be administered in the form of a transdermal delivery system, the administration of a therapeutic dose will, of course, be continuous rather than intermittent throughout the dosage regimen.

Compounds of the present invention may also be delivered by the use of monoclonal antibodies as individual carriers to which the compound molecules are coupled. The compounds of the present invention may also be coupled with soluble polymers as targetable drug carriers. Such polymers can include, but are not limited to polyvinylpyrrolidone, pyran copolymer, polyhydroxypropylmethacrylamidephenol, polyhydroxy-ethylaspartamidephenol, or polyethyl eneoxidepolylysine substituted with palmitoyl residue. Furthermore, the compounds of the present invention may be coupled to a class of biodegradable polymers useful in achieving controlled release of a drug, for example, to homopolymers and copolymers (which means polymers containing two or more chemically distinguishable repeating units) of lactide (which includes lactic acid d-, I- and meso lactide), glycolide (including glycolic acid), $\epsilon$-caprolactone, p-dioxanone (1,4-dioxan-2-one), trimethylene carbonate (1,3-dioxan-2-one), alkyl derivatives of trimethylene carbonate, $\delta$-valerolactone, $\beta$-butyrolactone, $\gamma$-butyrolactone, $\epsilon$-decalactone, hydroxybutyrate, hydroxyvalerate, 1,4-dioxepan-2-one (including its dimer 1,5,8,12-tetraoxacyclotetradecane-7,14-dione), 1,5-dioxepan-2-one, 6,6-dimethyl-1,4-dioxan-2-one, polyorthoesters, polyacetals, polydihydropyrans, polycyanoacrylates and cross-linked or amphipathic block copolymers of hydrogels and blends thereof.

Compounds of this invention may be administered in any of the foregoing compositions and dosage regimens or by means of those compositions and dosage regimens established in the art whenever treatment of integrin mediated disorders is required for a subject in need thereof.

The daily dose of a pharmaceutical composition of the present invention may be varied over a wide range from about 0.1 to 20,000 mg per adult human per day, however the dose will preferably be in the range of from about 1 to about 1,000 mg per adult human per day. For oral administration, the compositions are preferably provided in the form of tablets containing 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the subject to be treated. An effective amount of the drug is ordinarily supplied at a dosage level of from about 0.01 mg/kg/day to about 300 mg/kg/day. Particularly, the range is from about 0.5 to about 5.0 mg/kg of body weight per day; and more particularly, from about 1.0 to about 3.0 mg/kg of body weight per day. The compounds may be administered on a regimen of 1 to 4 times per day.

Optimal dosages to be administered may be readily determined by those skilled in the art, and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level.

Abbreviations used in the instant specification, particularly the Schemes and Examples, are as follows:

| | |
|---|---|
| Bn or Bzl | benzyl |
| Boc | tert-butoxycarbonyl |
| BOP-Cl | Bis(2-oxo-3-oxazolidinyl)phosphinic chloride |
| BSA | bovine serum albumin |
| CBZ | benzyloxycarbonyl |
| d | day(s) |
| DBC | 2,6-Dichlorobenzoylchloride |
| DMAP | 4-dimethylaminopyridine |
| DMF | N,N-dimethylformamide |
| DMSO | dimethylsulfoxide |
| DIPEA | Diisopropylethylamine |
| DMAP | Dimethylaminopyridine |
| EDC | ethyl dimethylaminopropyl-carbodiimide |
| EDTA | ethylenediaminetetraacetic acid |
| $Et_3N$ | triethylamine |

-continued

| | |
|---|---|
| EDAC | N-ethyl-N'-dimethylaminopropylcarbodiimide hydrochloride |
| Et₂O | Diethyl ether |
| EtOAc | Ethyl acetate |
| EtOH | Ethanol |
| h | hour |
| HBTU | O-Benzotiazol-1-yl-N,N,N',N'-tetramethyluronium hexafluorophosphate |
| HOBt | hydroxybenzotriazole hydrate |
| HATU | O-(7-azabenzotriazol-1-yl)-1,1,3,3-tetramethyluronium hexafluorophosphate |
| HPLC | High Performance Liquid Chromatography |
| HEPES | 4-(2-hydroxyethyl)-1-piperazine-ethanesulfonic acid |
| Me | methyl |
| MeOH | methanol |
| MeCN | acetonitrile |
| min | Minutes |
| MPK | milligrams per kilogram |
| NMM | N-methyl-morpholine |
| NT | not tested |
| PBS | Phosphate Buffer Solution |
| Ph | Phenyl |
| (o-tolyl)₃P | tri-o-tolylphosphine |
| Pd/C | palladium on activated carbon |
| Pd(OAc)₂ | palladium(II) acetate |
| Ph₃P | triphenylphosphine |
| PPT | precipitate |
| psi | pounds per square inch |
| rt | Room temperature |
| SDS | Sodium Dodecasulfate |
| TEA | Triethylamine |
| THF | Tetrahydrofuran |
| Thi | Thienyl |
| TMS | Tetramethylsilane |
| TFA | Trifluoroacetic acid |
| Tol | Toluene |

General Synthetic Methods

Representative compounds of the present invention can be synthesized in accordance with the general synthetic methods described below and are illustrated more particularly in the schemes that follow. Since the schemes are an illustration, the invention should not be construed as being limited by the chemical reactions and conditions expressed. The preparation of the various starting materials used in the schemes is well within the skill of persons versed in the art.

Scheme A describes the preparation of a lactam intermediate (A4) which may be used to prepare compounds of the present invention.

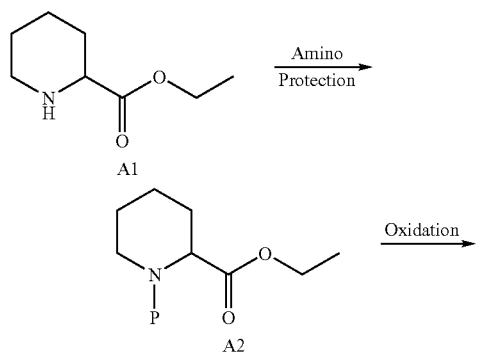

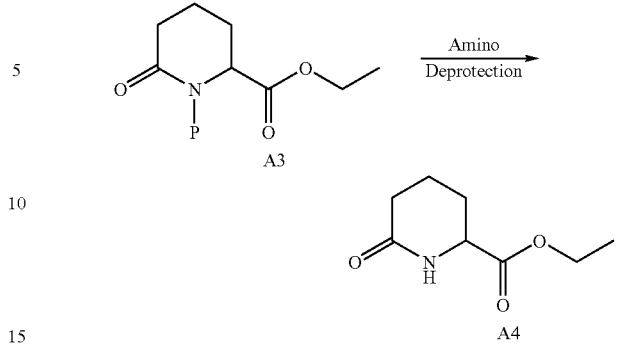

A cyclic amine of the formula A1 may be protected with a conventional amino protecting group (P) to give a compound of the formula A2, which may be oxidized with an oxidizing agent such as ruthenium oxide in the presence of a perchlorate salt or to give a protected lactam of the formula A3. The amino-protecting group may then be removed using conventional deprotective methods appropriate for a given P-group to give compounds of formula A4.

Scheme B describes the preparation of bicyclic triazole intermediates, which may be used to prepare compounds of the present invention.

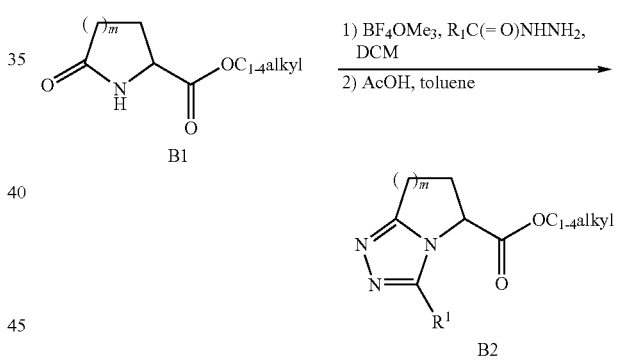

A lower alkyl ester of formula B1 may be converted to an iminoether. Subsequent reaction of the iminoether with an appropriately substituted hydrazide followed by treatment with acetic acid in toluene provides bicyclic triazole compounds of formula B2.

Scheme C describes the preparation of oxobicyclic triazole intermediates which may be used to prepare compounds of the present invention.

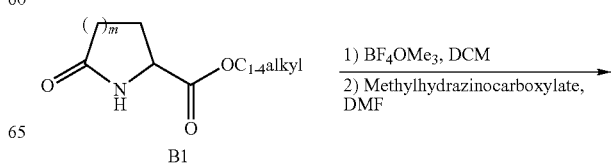

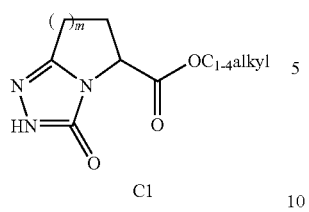

A compound of the formula B1 may be converted to an imino ether, and subsequently may be reacted with methylhydrazinocarboxylate in a solvent such as DMF to give an oxobicyclic triazole of formula C1.

Scheme D describes the synthesis of amino ester intermediates wherein R³ is an aryl or heteroaryl substituent as defined herein.

Scheme D

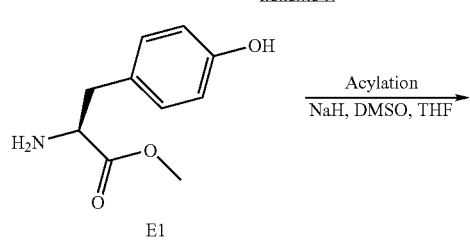

R³=aryl or heteroaryl Commercially available compounds of formula D1 may be coupled with an R³-substituted boronic acid in the presence of a palladium catalyst, followed conversion to its methyl ester to yield compounds of formula D2.

Scheme E describes the synthesis of compounds of the formula E2.

Scheme E

The hydroxyl functionality of compounds of the formula E1 may be acylated with an appropriately substituted isocyanate, carbamoyl chloride or the like to give carbamates of formula E2.

Scheme F describes the synthesis of compounds of the formula F3, which are used to prepare certain compounds of the present invention.

Scheme F

PG = protecting group

The amino functionality of compounds of formula F1 may be protected with a conventional amino protecting group (PG). The nitro group may be converted to its corresponding amine under reducing conditions such as in a hydrogen atmosphere in the presence of an appropriate transition metal catalyst, like palladium on carbon. Other suitable reaction conditions for the conversion of nitro groups to amines include subjection of a compound of formula F1 to zinc powder or tin chloride under basic conditions to yield compounds of formula F2. Compounds of formula F2 may be further derivatized via acylation or sulfonylation of the amino group using an appropriately substituted acid chloride, sulfonyl chloride or the like to give compounds wherein R³ may be an amide, sulfonamide, carbamate, or urea as defined herein. Deprotection of the amino group using conventional chemistry yields compounds of formula F3.

Scheme G describes the synthesis of certain compounds of the present invention.

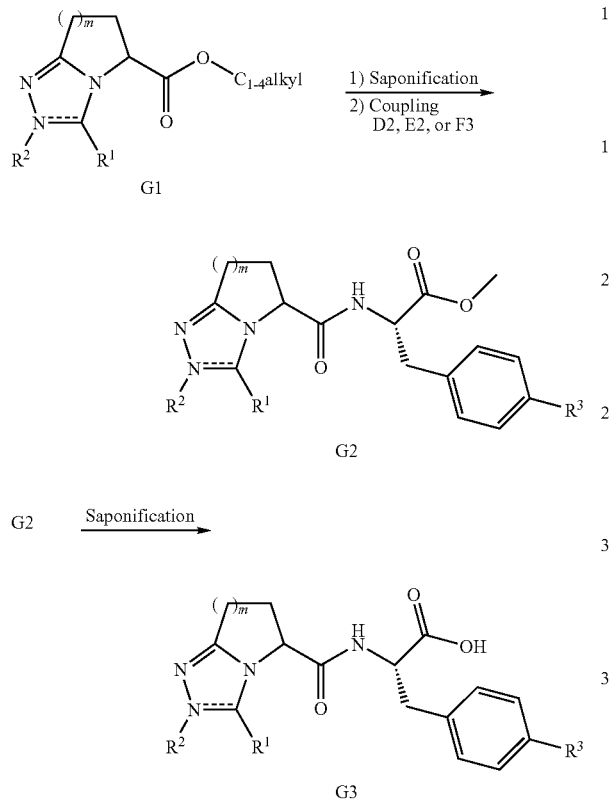

The ester of compounds of formula G1 may be converted to its corresponding carboxylic acid upon treatment with hydroxide. The carboxylic acid may then be coupled with the amine of a compound of the formula D2, E2, or F3 under standard coupling conditions to yield a compound of formula G2. Standard coupling conditions include a coupling agent such as HBTU, an activating agent such as HOBt, an appropriate base, and solvent. Saponification of compounds of formula G2 under basic conditions provides compounds of formula G3.

Compounds of formula G2 wherein $R^1$ is oxo and $R^2$ is hydrogen may be further elaborated by the alkylation of the $N_1$ nitrogen to yield additional compounds of the present invention where the $R^2$ substituents are as defined herein. Standard amine alkylation conditions involve the displacement of a leaving group (iodide, bromide, sulfonate, chloride) from a functionalized precursor of $R^2$ under basic conditions. The resulting compounds are those of formula G3 wherein $R^2$ is a substituent other than hydrogen as previously defined.

Scheme H describes the synthesis of certain compounds of the present invention.

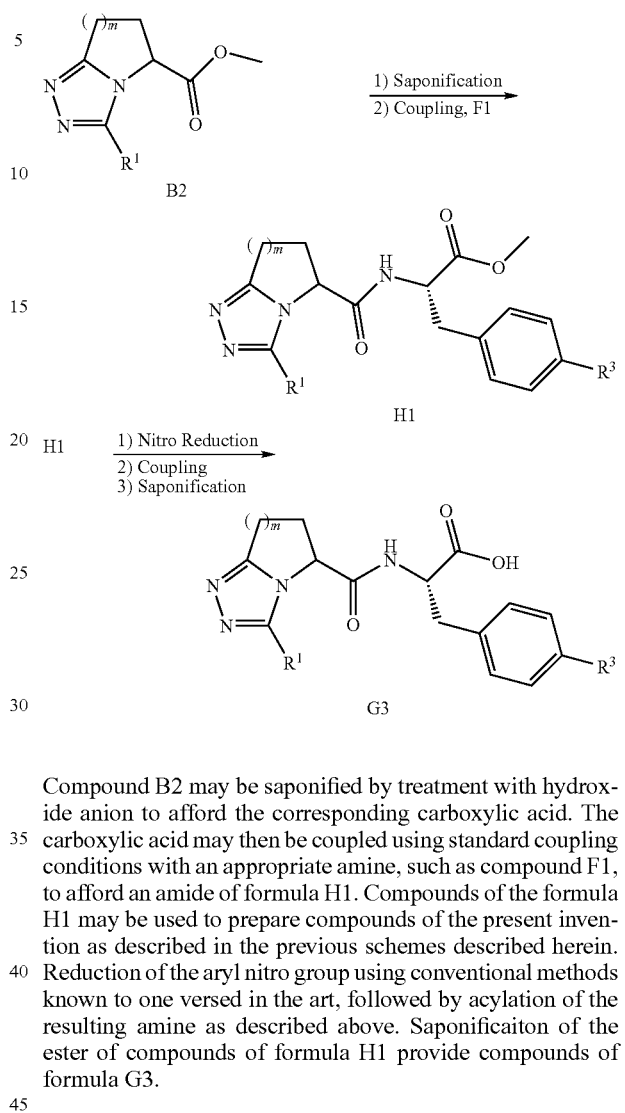

Compound B2 may be saponified by treatment with hydroxide anion to afford the corresponding carboxylic acid. The carboxylic acid may then be coupled using standard coupling conditions with an appropriate amine, such as compound F1, to afford an amide of formula H1. Compounds of the formula H1 may be used to prepare compounds of the present invention as described in the previous schemes described herein. Reduction of the aryl nitro group using conventional methods known to one versed in the art, followed by acylation of the resulting amine as described above. Saponificaiton of the ester of compounds of formula H1 provide compounds of formula G3.

SPECIFIC EXAMPLES

Specific compounds which are representative of this invention were prepared as per the following examples and reaction sequences; the examples and the diagrams depicting the reaction sequences are offered by way of illustration, to aid in the understanding of the invention and should not be construed to limit in any way the invention set forth in the claims which follow thereafter. The instant compounds may also be used as intermediates in subsequent examples to produce additional compounds of the present invention. No attempt has been made to optimize the yields obtained in any of the reactions. One skilled in the art would know how to increase such yields through routine variations in reaction times, temperatures, solvents and/or reagents.

Reagents were purchased from commercial sources. Nuclear magnetic resonance (NMR) spectra for hydrogen atoms were measured in the indicated solvent with (TMS) as the internal standard on a Bruker AM-360 (360 MHz) spectrometer. The values are expressed in parts per million down field from TMS. The mass spectra (MS) were determined on a Micromass Plafform LC spectrometer or an Agilent LC spectrometer using electrospray techniques. Microwave accelerated reactions were performed using either a CEM Discover or a Personal Chemistry Smith Synthesizer microwave instrument. Stereoisomeric compounds may be characterized as racemic mixtures or as separate diastereomers and enantiomers thereof using X-ray crystallography and other methods known to one skilled in the art. Unless otherwise noted, the materials used in the examples were obtained from readily available commercial suppliers or synthesized by standard methods known to one skilled in the art of chemical synthesis. The substituent groups, which vary between examples, are hydrogen unless otherwise noted.

Example 1

3-(4-Dimethylcarbamoyloxy-phenyl)-2-(S)-[(3-phenyl-5,6,7,8-tetrahydro-[1,2,4]triazolo[4,3-a]pyridine-5-carbonyl)-amino]-propionic acid (Cpd 1)

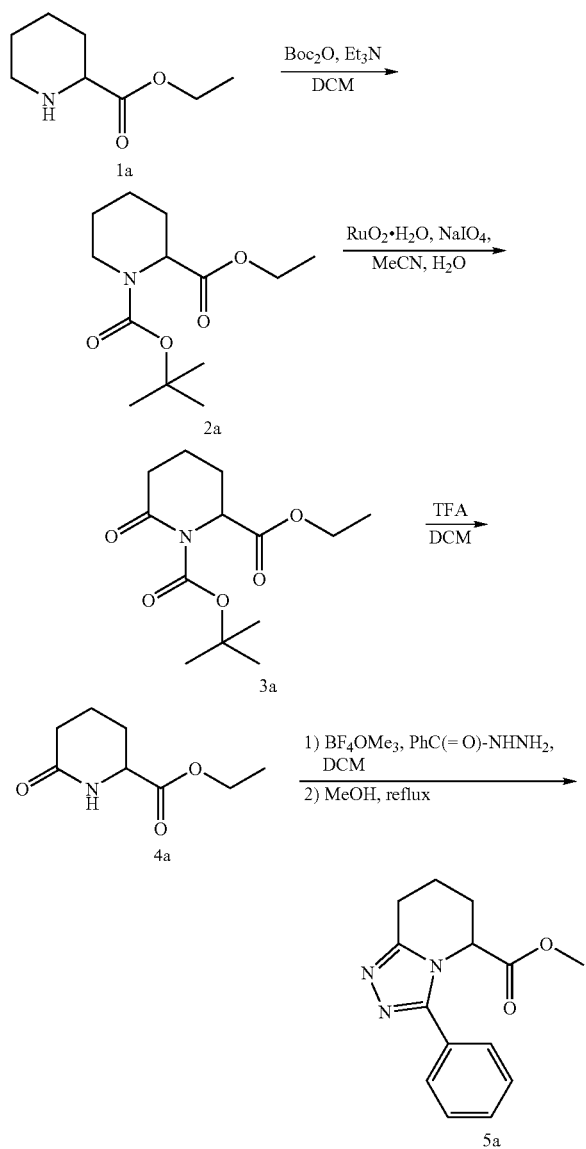

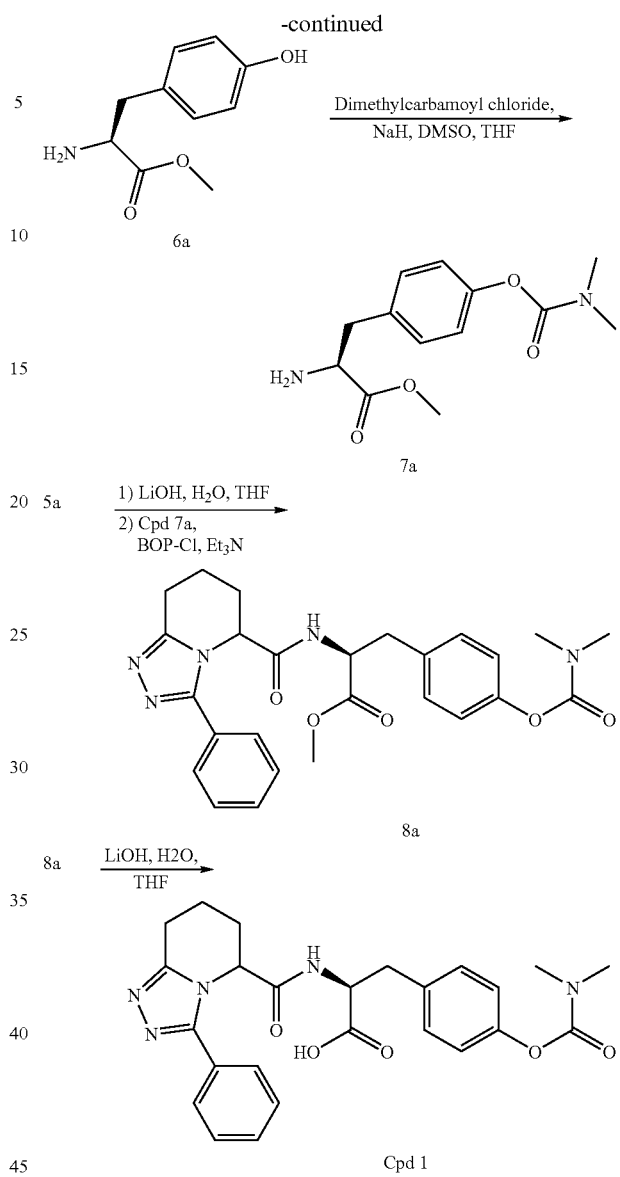

Procedure 1

Compound 1a (5.00 g, 0.032 mol) was dissolved in dry DCM (160 mL) containing TEA (6.0 mL, 0.043 mol) and di-tert-butyl dicarbonate (6.90 g, 0.032 mol) was added in 3 portions. The reaction was stirred for 18 h at room temperature. The reaction mixture was diluted with DCM (200 mL) and washed with 1.0 N HCl. The organic layers were combined and dried over $MgSO_4$, filtered through CELITE®, and concentrated in vacuo to give Compound 2a as a viscous oil. $^1$H NMR (300 MHz, $CDCl_3$) δ 4.70-4.86 (m, 1H), 4.19 (q, J=7.1 Hz, 2H), 3.94-3.99 (m, 1H), 2.87-2.97 (m, 1H), 2.19-2.22 (m, 1H), 1.70-1.72 (m, 3H), 1.67-1.69 (m, 2H), 1.45 (s, 9H), and 1.27 (t, J=7.2 Hz, 3H); MS ($ES^+$) 258.

Procedure 2

Compound 2a (8.20 g, 0.032 mol) was dissolved in MeCN (20 mL) and $H_2O$ (92 mL). Sodium periodate (19.8 g, 0.093 mol) was added followed by ruthenium (IV) oxide hydrate (0.13 g, 0.001 mol). The mixture was stirred at room temperature for 24 h followed by extraction with EtOAc (500 mL). The organic layer was then treated with isopropanol (100 mL) at room temperature for 2 h. The mixture was then filtered through CELITE® and the filtrate washed with saturated aqueous NaCl. The organic layer was dried over MgSO$_4$, filtered through CELITE®, and concentrated in vacuo to give Compound 3a as a viscous oil. The oil was dissolved in TFA (14.0 mL), DCM (56.0 mL), and stirred at room temperature for 1 h. The mixture was concentrated in vacuo to give Compound 4a as a viscous oil. $^1$H NMR (300 MHz, CDCl$_3$) δ 8.32 (br s, 1H), 4.26 (q, J=7.2 Hz, 2H), 4.15-4.19 (m, 1H), 2.47-2.52 (m, 2H), 2.20-2.27 (m, 1H), 1.82-1.96 (m, 3H), and 1.31 (t, J=7.1 Hz, 3H); MS (ES$^+$) 172.

Procedure 3

Compound 4a (0.64 g, 0.004 mol) was dissolved in DCM (12.5 mL) and treated with trimethyloxonium tetrafluoroborate (0.64 g, 0.004 mol). The mixture was stirred at room temperature for 24 h. Benzoic hydrazide (0.58 g, 0.004 mol) was added and the mixture was stirred at room temperature for 24 h. The mixture was concentrated in vacuo and dissolved in MeOH (16.0 mL). The solution was heated to reflux using a Dean-Stark trap for 24 h. The mixture was cooled to room temperature and concentrated in vacuo. The residue was purified by column chromatography (silica gel, using a gradient of DCM:MeOH 98:2 to 92:8) to provide Compound 5a. $^1$H NMR (300 MHz, CDCl$_3$) δ 8.32 (br s, 1H), 7.81 (d, J=1.8 Hz, 2H), 7.39-7.50 (m, 3H), 4.22 (q, J=6.6 Hz, 2H), 4.13-4.20 (m, 1H), 2.33-2.39 (m, 2H), 2.13-2.21 (m, 1H), 1.78-1.88 (m, 3H), and 1.29 (t, J=7.1 Hz, 3H); MS (ES$^+$) 272.

Procedure 4

L-Tyrosine methyl ester (compound 6a, 35.0 g, 0.179 mol) was dissolved in THF (900 mL) and DMSO (70 mL). The mixture was cooled using an acetone/dry ice bath to 0° C. Sodium hydride (5.0 g, 0.198 mol) was added in three portions. The mixture was stirred for 30 min in the acetone/dry ice bath and then cooled to −10° C. Dimethylcarbamoyl chloride (16.5 mL, 0.179 mol) was added dropwise and stirred at 0° C. for 1 h. The reaction was quenched with 1N NaOH and extracted with EtOAc. The organic layers were dried over MgSO$_4$, filtered through CELITE®, and concentrated in vacuo to give Compound 7a. MS (ES$^+$) 267.

Procedure 6

Compound 5a (0.22 g, 0.0008 mol) was dissolved in THF (4.0 mL). LiOH (0.06 g, 0.001 mol) was dissolved in water (8.0 mL) and added to the THF mixture. After stirring at room temperature for 30 min the mixture was acidified with 1N HCl and extracted with DCM. The organic layers were dried over MgSO$_4$, filtered through CELITE®, and concentrated in vacuo. The crude oil (0.13 g) was dissolved in DCM (1.0 mL). BOP-Cl (0.20 g, 0.0008 mol) and Et$_3$N (0.14 mL, 0.001 mol) were added and the mixture stirred at room temperature for 15 min. Compound 7a (0.16 g, 0.0006 mol) was added and the mixture stirred for 18 h. The mixture was diluted with DCM and washed with 1N HCl. The organic layers were dried over MgSO$_4$, filtered through CELITE®, and concentrated in vacuo. The crude oil was dissolved in THF (0.2 mL) and stirred at room temperature. LiOH (5.0 mg, 0.12 mmol) was dissolved in H$_2$O (0.4 mL) and added to the THF solution. After stirring for 1 h at room temperature the mixture was acidified with 1N HCl and extracted with DCM. The organic layers were dried using MgSO$_4$, filtered through CELITE®, and concentrated in vacuo. The crude oil was purified using a Gilson HPLC containing a Kromasil column (10 u, 100 Å C18, column length 250×50 mm, gradient 90:10 H$_2$O: MeCN) to give the title compound (1). $^1$H NMR (300 MHz, CDCl$_3$) δ 7.48-7.62 (m, 5H), 7.02-7.22 (m, 4H), 5.10-5.21 (m, 1H), 4.53-4.65 (m, 1H), 3.31 (s, 3H), 3.30 (s, 3H), 2.98-3.15 (m, 4H), and 2.03-2.34 (m, 4H); MS (ES$^+$) 478.

Example 2

2-(S)-[(3-Benzyl-5,6,7,8-tetrahydro-[1,2,4]triazolo [4,3-a]pyridine-5-carbonyl)-amino]-3-(4-dimethylcarbamoyloxy-phenyl)-propionic acid (Cpd 2)

Compound 2 was prepared using the method provided in Example 1, substituting phenylacetic hydrazide (0.54 g) for benzoic hydrazide in Procedure 3. Compound 2: $^1$H NMR (300 MHz, CDCl$_3$) δ 7.23-7.32 (m, 7H), 7.00-7.12 (m, 2H), 4.98-5.02 (m, 1H), 4.05-4.13 (m, 1H), 3.32 (s, 3H), 3.30 (s, 3H), 3.10 (2Hs,), 2.95-3.00 (m, 2H), 2.30-2.35 (m, 2H), and 1.81-2.12 (m, 4H); MS (ES$^+$) 492.

Example 3

2-(S)-[(3-Benzyl-6,7-dihydro-5H-pyrrolo[2,1-c][1,2,4]triazole-5-(S)-carbonyl)-amino]-3-(4-dimethylcarbamoyloxy-phenyl)-propionic acid (Cpd 3)

Compound 3 was prepared was prepared using the method provided in Example 1, substituting (S)-ethyl 2-pyrrolidone-5-carboxylate (2.05 g) for Compound 4a and phenylacetic hydrazide (2.17 g) for benzoic hydrazide in Procedure 3. Compound 3: $^1$H NMR (300 MHz, CDCl$_3$) δ 7.23-7.34 (m, 5H), 6.95-7.12 (m, 4H), 4.77-4.89 (m, 1H), 4.364.44 (m, 1H), 3.76 (s, 2H), 3.06-3.18 (m, 2H), 3.02 (s, 3H), 2.99 (s, 3H), and 2.69-2.88 (m, 4H): MS (ES$^+$) 478.

Example 4

2-(S)-[(3-Benzyl-6,7-dihydro-5H-pyrrolo[2,1-c][1,2,4]triazole-5-(S)-carbonyl)-amino]-3-[4-(2,6-dichloro-benzoylamino)-phenyl]-propionic acid (Cpd 4)

Compound 4 was prepared was prepared using the method provided in Example 1, substituting (S)-ethyl 2-pyrrolidone-5-carboxylate (2.05 g) for Compound 4a and phenylacetic hydrazide (2.17 g) for benzoic hydrazide in Procedure 3; and substituting 2-amino-3-(4-nitro-phenyl)-propionic acid methyl ester (1.95 g) for Compound 7a in Procedure 6 to give 2-(S)-[(3-Benzyl-6,7-dihydro-5H-pyrrolo[2,1-c][1,2,4]triazole-5-(S)-carbonyl)-amino]-3-(4-nitro-phenyl)-propionic acid.

Procedure 7

2-(S)-[(3-Benzyl-6,7-dihydro-5H-pyrrolo[2,1-c][1,2,4] triazole-5-(S)-carbonyl)-amino]-3-(4-nitro-phenyl)-propionic acid (2.8 g, 0.006 mol) was dissolved in EtOAc (30 mL) and treated with 10% Pd/C (0.28 g) and hydrogen (50 psi) for 24 h. The mixture was filtered through CELITE® and purified by flash chromatography (98:2-92:8 DCM:MeOH gradient). The solid (100.0 mg, 0.239 mmol) was dissolved in DCM (1.2 mL) and treated with Et$_3$N (0.1 mL, 0.717 mmol). A portion of 2,6-dichlorobenzoyl chloride (0.04 mL, 0.272 mmol) was added and the mixture was stirred at room temperature for 24 h. The mixture was diluted with DCM and washed with 1N NaOH. The organic layers were combined, dried over MgSO$_4$, filtered through CELITE®, and concentrated in vacuo. The crude solid was dissolved in THF (1.2 mL), treated with a solution of LiOH (15.0 mg, 0.358 mmol) in H$_2$O (2.4 mL), and stirred at room temperature for 1 h. The mixture was treated with 1N HCl and extracted with DCM.

The organic layers were combined, dried over $MgSO_4$, filtered through CELITE®, and concentrated in vacuo. The crude oil was purified using a reversed phase Gilson containing a Kromasil column (10 u, 100 Å C18, column length 250×50 mm, gradient 90:10 to 0:100 $H_2O$:MeCN) to give the title compound 4. $^1$H NMR (300 MHz, $CDCl_3$) δ 7.09-7.68 (1m, 2H), 4.60-4.78 (m, 1H), 4.14-4.19 (m, 1H), 3.79 (s, 2H), 3.22-3.34 (m, 2H), 3.19 (s, 3H), 3.07 (s, 3H), and 2.74-2.96 (m, 4H): MS ($ES^+$) 579.

Example 5

2-(S)-[(3-Benzyl-6,7-dihydro-5H-pyrrolo[2,1-c][1,2,4]triazole-5-(S)-carbonyl)-amino]-3-{4-[(naphthalene-1-carbonyl)-amino]-phenyl}-propionic acid (Cpd 5)

Compound 5 was prepared using the method provided in Example 4, substituting 1-naphthoyl chloride (0.04 mL) for 2,6-dichlorobenzoyl chloride in Procedure 7. Compound 5: $^1$H NMR (300 MHz, $CDCl_3$) δ 9.09 (m, 1H), 7.82-8.21 (m, 6H) 7.08-7.75 (m, 9H), 4.74-4.83 (m, 1H), 4.04-4.14 (m, 1H), 3.85 (s, 2H), 3.32-3.43 (m, 2H), and 2.81-3.13 (m, 4H): MS ($ES^+$) 560.

Example 6

2-(S)-[(3-Benzyl-6,7-dihydro-5H-pyrrolo[2,1-c][1,2,4]triazole-5-(S)-carbonyl)-amino]-3-{4-[(naphthalene-2-carbonyl)-amino]-phenyl}-propionic acid (Cpd 6)

Compound 6 was prepared using the method provided in Example 4, substituting 2-naphthoyl chloride (0.04 mL) for 2,6-dichlorobenzoyl chloride in Procedure 7. Compound 6: $^1$H NMR (300 MHz, $CDCl_3$) δ 8.35 (s, 1H), 7.87-8.02 (m, 5H) 7.60-7.75 (m, 4H), 7.08-7.37 (m, 6H), 4.824.90 (m, 2H), 3.70-3.93 (m, 2H), and 2.84-3.33 (m, 6H): MS ($ES^+$) 560.

Example 7

2-(S)-[(3-Benzyl-6,7-dihydro-5H-pyrrolo[2,1-c][1,2,4]triazole-5-(S)-carbonyl)-amino]-3-{4-[(2-ethoxy-naphthalene-1-carbonyl)-amino]-phenyl}-propionic acid (Cpd 7)

Compound 7 was prepared using the method provided in Example 4, substituting 2-ethoxy-1-naphthoyl chloride (0.062 g) for 2,6-dichlorobenzoyl chloride in Procedure 7. Compound 7: $^1$H NMR (300 MHz, $CDCl_3$) δ 9.02 (m, 1H), 7.69-7.99 (m, 6H) 7.29-7.47 (m, 6H), 7.05-7.17 (m, 2H), 4.75-4.83 (m, 2H), 4.24 (q, J=7.1 Hz, 2H), 3.92-3.98 (m, 2H), 2.83-3.43 (m, 6H), and 1.34 (t, J=7.0 Hz, 3H): MS ($ES^+$) 604.

Example 8

2-(S)-[(3-Benzyl-6,7-dihydro-5H-pyrrolo[2,1-c][1,2,4]triazole-5-(S)-carbonyl)-amino]-3-{4-[(9-oxo-9H-fluorene-4-carbonyl)-amino]-phenyl}-propionic acid (Cpd 8)

Compound 8 was prepared using the method provided in Example 4, substituting 9-fluorenone-4-carbonyl chloride (0.064 g) for 2,6-dichlorobenzoyl chloride in Procedure 7. Compound 8: $^1$H NMR (300 MHz, $CDCl_3$) δ 7.67-7.76 (m, 6H) 7.29-7.50 (m, 8H), 7.09-7.20 (m, 2H), 4.73-4.83 (m, 2H), 3.91-4.08 (m, 2H), and 2.98-3.37 (m, 6H): MS ($ES^+$) 612.

Example 9

2-(S)-[(3-Benzyl-6,7-dihydro-5H-pyrrolo[2,1-c][1,2,4]triazole-5-(S)-carbonyl)-amino]-3-{4-[(3,5-dichloro-pyridine-4-carbonyl)-amino]-phenyl}-propionic acid (Cpd 9)

Compound 9 was prepared using the method provided in Example 4, substituting 3,5-dichloroisonicotinic chloride (0.055 g) for 2,6-dichlorobenzoyl chloride. Compound 9: $^1$H NMR (300 MHz, $CDCl_3$) δ 8.65 (s, 2H), 7.68 (d, J=8.48 Hz, 2H), 7.37 (d, J=8.49 Hz, 2H), 7.27-7.29 (m, 3H), 7.05-7.07 (m, 2H), 4.69-4.87 (m, 2H), 3.87-4.00 (m, 2H), and 2.94-3.33 (m, 6H): MS ($ES^+$) 580.

Example 10

2-(S)-[(3-Benzyl-6,7-dihydro-5H-pyrrolo[2,1-c][1,2,4]triazole-5-(S)-carbonyl)-amino]-3-[4-(5-methoxy-2-methyl-3-oxo-2,3-dihydro-pyridazin-4-yl)-phenyl]-propionic acid (Cpd 17)

3-Phenyl-6,7-dihydro-5H-pyrrolo[2,1-c][1,2,4]triazole-5-carboxylic acid methyl ester was prepared using the method provided in Procedure 3, substituting (S)-ethyl 2-pyrrolidone-5-carboxylate (2.05 g) for Compound 4a and substituting phenylacetic hydrazide (2.17 g) for benzoic hydrazide.

Procedure 8

4-Borono-L-phenylalanine (0.30 g, 1.0 mmol), 4-Bromo-5-methoxy-2-methyl-2H-pyridazin-3-one (0.35 g, 1.0 mmol), tetrakistriphenylphosphine palladium(0) (0.09 g), and 2.0 M aqueous sodium carbonate (3.0 mL) were refluxed in MeCN (900 mL) for 4 d. The mixture was acidified with 2.0 N HCl and treated with MeOH. The solid was filtered off and the mixture was concentrated in vacuo. The crude solid was purified using a Gilson HPLC containing a Kromasil column (10 u, 100 Å C18, column length 250×50 mm, gradient 100:0 to 10:90 $H_2O$:MeCN) to give 2-(S)-Amino-3-[4-(5-methoxy-2-methyl-3-oxo-2,3-dihydro-pyridazin-4-yl)-phenyl]-propionic acid. MS ($ES^+$) 304.

Procedure 9

2-(S)-Amino-3-[4-(5-methoxy-2-methyl-3-oxo-2,3-dihydro-pyridazin-4-yl)-phenyl]-propionic acid (0.40 g, 1.0 mmol) was dissolved in MeOH (2.6 mL). Dimethoxypropane (0.26 mL) and 1N HCl in dioxane (0.33 mL) were added and stirred at room temperature for 24 h. The mixture was concentrated in vacuo to give 2-Amino-3-[4-(5-methoxy-2-methyl-3-oxo-2,3-dihydro-pyridazin-4-yl)-phenyl]-propionic acid methyl ester. MS ($ES^+$) 318.

Using the method described in Procedure 6, substituting 2-(S)-Amino-3-[4-(5-methoxy-2-methyl-3-oxo-2,3-dihydro-pyridazin-4-yl)-phenyl]-propionic acid methyl ester (0.57 g) for Compound 7a, 2(S)-[(3-Benzyl-6,7-dihydro-5H-pyrrolo[2,1-c][1,2,4]triazole-5-(S)-carbonyl )-amino]-3-[4-(5-methoxy-2-methyl-3-oxo-2,3-dihydro-pyridazin-4-yl)-phenyl]-propionic acid methyl ester was prepared in crude form.

The crude solid was dissolved in THF, treated with a solution of LiOH in $H_2O$, and stirred at room temperature for 1 h. The mixture was treated with 1N HCl and extracted with DCM. The organic layers were combined, dried over $MgSO_4$, filtered through CELITE®, and concentrated in vacuo. The crude oil was purified using a Gilson HPLC containing a Kromasil column (10 u, 100 Å C18, column length 250×50 mm, gradient 90:10 to 10:90 $H_2O$:MeCN) to give the title compound 17. $^1$H NMR (300 MHz, $CD_3OD$) δ 8.12 (s, 1H), 7.23-7.45 (m, 7H), 7.06-7.12 (m, 2H), 4.864.95 (m, 2H), 3.84 (s, 3H), 3.76 (s, 2H), 3.31 (s, 3H), and 2.82-3.23 (m, 6H): MS (ES+) 529.

Example 11

3-[4-(2,6-Dichloro-benzoylamino)-phenyl]-2-(S)-[(3-oxo-2,5,6,7-tetrahydro-3H-pyrrolo[2,1-c][1,2,4]triazole-5-(S)-carbonyl)-amino]-propionic acid (Cpd 18)

Procedure 10

A portion of (S)-methyl 2-pyrrolidone-5-carboylate (3.00 g, 0.021 mol) was dissolved in DCM (105 mL) and treated with trimethyloxonium tetrafluoroborate (3.10 g, 0.021 mol). The mixture was stirred at room temperature for 24 h. The mixture was concentrated in vacuo. The oil was dissolved in DMF (100 mL). Methyl hydrazinocarboxylate (2.00 g, 0.022 mol) was added and the solution was heated to reflux using a Dean-Stark trap for 24 h. The mixture was cooled to room temperature and concentrated in vacuo. The residue was purified by column chromatography (silica gel, using a gradient of DCM:MeOH 95:5 to 90:10) to provide 3-Oxo-2,5,6,7-tetrahydro-3H-pyrrolo[2,1-c][1,2,4]triazole-5-carboxylic acid methyl ester. $^1$H NMR (300 MHz, CDCl$_3$) δ 4.68-4.72 (m, 1H), 3.82 (s, 3H), 2.75-2.99 (m, 4H); MS (ES+) 184.

Procedure 11

3-Oxo-2,5,6,7-tetrahydro-3H-pyrrolo[2,1-c][1,2,4]triazole-5-carboxylic acid methyl ester (0.50 g, 2.7 mmol) was dissolved in THF (3.0 mL). LiOH (0.14 g, 3.3 mmol) was dissolved in water (3.0 mL), which was added to the THF mixture and stirred at room temperature for 30 min. The mixture was acidified with 1N HCl and extracted with DCM. The organic layers were dried over MgSO$_4$, filtered through CELITE®, and concentrated in vacuo to give 3-Oxo-2,5,6,7-tetrahydro-3H-pyrrolo[2,1-c][1,2,4]triazole-5-carboxylic acid.

Procedure 12

The crude oil of 3-Oxo-2,5,6,7-tetrahydro-3H-pyrrolo[2,1-c][1,2,4]triazole-5-carboxylic acid (0.46 g, 2.7 mmol) was dissolved in MeCN (27.0 mL) and HOBt (0.406 g, 3.0 mmol), HBTU (2.1 g, 6.0 mmol), and Et$_3$N (0.84 mL, 6.0 mmol) were added and the mixture stirred at room temperature for 15 min. 2-(S)-Amino-3-[4-(2,6-dichloro-benzoylamino)-phenyl]-propionic acid methyl ester (1.6 g, 3.3 mmol) and the mixture stirred at room temperature for 18 h. The mixture was diluted with DCM and washed with 1N HCl. The organic layers were dried over MgSO$_4$, filtered through CELITE®, and concentrated in vacuo. The crude oil was dissolved in THF (1.5 mL) and stirred at room temperature. LiOH (20.0 mg, 0.48 mmol) was dissolved in H$_2$O (3.0 mL) and added to the THF solution. After stirring for 1 h at room temperature the mixture was acidified with 1N HCl and extracted with DCM. The organic layers were dried over MgSO$_4$, filtered through CELITE®, and concentrated in vacuo. The crude oil was purified using a reversed phase Gilson containing a Kromasil column (10 u, 100 Å C18, column length 250×50 mm, gradient 90:10 H$_2$O:MeCN) to give the title compound (18). $^1$H NMR (300 MHz, CDCl$_3$) δ 7.58 (d, J=8.4 Hz, 2H), 7.36-7.49 (m, 3H), 7.27 (d, J=8.4 Hz, 2H), 4.66-4.73 (m, 2H), 3.24-3.31 (m, 1H), 3.00-3.24 (m, 1H), 2.72-2.86 (m, 3H), and 2.55-2.61 (m, 1H); MS (ES+) 505.

Example 12

3-{4-[(3,5-Dichloro-pyridine-4-carbonyl)-amino]-phenyl}-2-(S)-[(3-oxo-2,5,6,7-tetrahydro-3H-pyrrolo[2,1-c][1,2,4]triazole-5-(S)-carbonyl)-amino]-propionic acid (Cpd 20)

Using the method described in Example 11, substituting 2-amino-3-{4-[(3,5-dichloro-pyridine-4-carbonyl)-amino]-phenyl}-propionic acid methyl ester (0.15 g) for 2-amino-3-[4-(2,6-dichloro-benzoylamino)-phenyl]-propionic acid methyl ester in Procedure 12. Compound 20: $^1$H NMR (300 MHz, CDCl$_3$) δ 8.67 (s, 2H), 7.60 (d, J=8.4 Hz, 2H), 7.31 (d, J=8.4 Hz, 2H), 4.68-4.75 (m, 2H), 3.27-3.33 (m, 1H), 3.03-3.25 (m, 1H), 2.75-2.92 (m, 3H), and 2.57-2.65 (m, 1H): MS (ES+) 506.

Example 13

2-(S)-[(2-Benzyl-3-oxo-2,5,6,7-tetrahydro-3H-pyrrolo[2,1-c][1,2,4]triazole-5-(S)-carbonyl)-amino]-3-[4-(2,6-dichloro-benzoylamino)-phenyl]-propionic acid (Cpd 19)

Procedure 13

3-[4-(2,6-Dichloro-benzoylamino)-phenyl]-2-(S)-[(3-oxo-2,5,6,7-tetrahydro-3H-pyrrolo[2,1-c][1,2,4]triazole-5-(S)-carbonyl)-amino]-propionic acid methyl ester (0.12 g, 0.2 mmol) was dissolved in MeCN (1.2 mL). Potassium carbonate (0.05 g, 0.4 mmol) and benzyl bromide (0.03 mL, 0.3 mmol) were added to the solution. The mixture was refluxed for 24 h, then cooled to room temperature and filtered through CELITE®. The filtrate was concentrated in vacuo. The crude oil was dissolved in THF (1.3 mL) and stirred at room temperature. LiOH (20.0 mg, 0.48 mmol) was dissolved in H$_2$O (2.6 mL) and added to the THF solution. After stirring for 1 h at room temperature the mixture was acidified with 1N HCl and extracted with DCM. The organic layers were dried over MgSO$_4$, filtered through CELITE®, and concentrated in vacuo. The crude oil was purified using a Gilson HPLC containing a Kromasil column (10 u, 100 Å C18, column length 250×50 mm, gradient 90:10 H$_2$O:MeCN) to give Compound 18. $^1$H NMR (300 MHz, CDCl$_3$) δ 7.23-7.60 (m, 12H), 5.10-5.38 (m, 2H), 4.70-4.82 (m, 2H), and 2.73-3.27 (m, 6H): MS (ES+) 595.

Example 14

2-(S)-[(2-Benzyl-3-oxo-2,5,6,7-tetrahydro-3H-pyrrolo[2,1-c][1,2,4]triazole-5-(S)-carbonyl)-amino]-3-{4-[(3,5-dichloro-pyridine-4-carbonyl)-amino]-phenyl}-propionic acid (Cpd 21)

Using the method described in Procedure 13, substituting 3-{4-[(3,5-Dichloro-pyridine-4-carbonyl)-amino]-phenyl}-2-(S)-[(3-oxo-2,5,6,7-tetrahydro-3H-pyrrolo[2,1-c][1,2,4]triazole-5-(S)-carbonyl)-amino]-propionic acid methyl ester (0.08 g) for 3-[4-(2,6-Dichloro-benzoylamino)-phenyl]-2-(S)-[(3-oxo-2,5,6,7-tetrahydro-3H-pyrrolo[2,1-c][1,2,4]triazole-5-(S)-carbonyl)-amino]-propionic acid methyl ester, the title compound 21 was prepared. $^1$H NMR (300 MHz, CDCl$_3$) δ 8.61 (s, 2H), 7.16-7.63 (m, 9H), 5.11-5.48 (m, 2H), 4.56-

4.87 (m, 2H), 3.30-3.34 (m, 1H), 2.88-3.08 (m, 4H), and 2.73-2.76 (m, 1H): MS (ES+) 596.

Example 15

3-[4-(2,6-Dichloro-benzoylamino)-phenyl]-2-(S)-[(3-propyl-6,7-dihydro-5H-pyrrolo[2,1-c][1,2,4]triazole-5-(S)-carbonyl)-amino]-propionic acid (Cpd 10)

Using the method described in Example 1, substituting (S)-methyl 2-pyrrolidone-5-carboxylate (1.0 g) for Compound 4a, butyric acid hydrazide (0.76 g) for benzoic hydrazide in Procedure 3 and substituting 2-(S)-amino-3-[4-(2,6-dichloro-benzoylamino)-phenyl]-propionic acid methyl ester (0.50 g) for Compound 7a in Procedure 6, Compound 10 was prepared. $^1$H NMR (300 MHz, CDCl$_3$) δ 7.62-7.68 (m, 2H), 7.43-7.52 (m, 3H), 7.29-7.35 (m, 2H), 4.80-4.85 (m, 2H), 2.95-3.26 (m, 6H), 2.84 (t, J=7.7 Hz, 1H), 2.54 (t, J=7.2 Hz, 1H), 1.58-1.78 (m, 2H), and 1.02 (t, J=7.3 Hz, 3H): MS (ES+) 531.

Example 16

2-(S)-{[3-(Benzyloxycarbonylamino-methyl)-6,7-dihydro-5H-pyrrolo[2,1-c][1,2,4]triazole-5-(S)-carbonyl]-amino}-3-[4-(2,6-dichloro-benzoylamino)-phenyl]-propionic acid (Cpd 11)

Using the method described in Example 1, substituting (S)-methyl 2-pyrrolidone-5-carboxylate (0.64 g) for Compound 4a, hydrazinocarbonylmethyl-carbamic acid benzyl ester (1.0 g) for benzoic hydrazide in Procedure 3 and substituting 2-(S)-amino-3-[4-(2,6-dichloro-benzoylamino)-phenyl]-propionic acid methyl ester (0.50 g) for Compound 7a in Procedure 6, Compound 11 was prepared. $^1$H NMR (300 MHz, CDCl$_3$) δ 7.29-7.63 (m, 12H), 5.11 (s, 2H), 4.73-4.89 (m, 2H), 4.33 (s, 1H), and 2.95-3.41 (m, 6H): MS (ES+) 652.

Example 17

3-[4-(2,6-Dichloro-benzoylamino)-phenyl]-2-(S)-[(3-thiophen-3-ylmethyl-6,7-dihydro-5H-pyrrolo[2,1-c][1,2,4]triazole-5-(S)-carbonyl)-amino]-propionic acid (Cpd 12)

Using the method described in Example 1, substituting (S)-methyl 2-pyrrolidone-5-carboxylate (1.09 g) for Compound 4a, thiophen-3-yl-acetic acid hydrazide (1.19 g) for benzoic hydrazide in Procedure 3 and substituting 2-(S)-amino-3-[4-(2,6-dichloro-benzoylamino)-phenyl]-propionic acid methyl ester (0.50 g) for Compound 7a in Procedure 6, Compound 12 was prepared. $^1$H NMR (300 MHz, CDCl$_3$) δ 7.61 (d, J=8.4 Hz, 2H), 7.47-7.56 (m, 4H), 7.45 (s, 1H), 7.29 (d, J=8.4 Hz, 2H), 6.98 (d, J=4.9 Hz, 1H), 4.81-4.86 (m, 1H), 4.72-4.76 (m, 1H), 4.81-4.86 (m, 1H), 3.33-3.41 (m, 2H), 4.81-4.86 (m, 1H), 2.93-3.05 (m, 4H), and 2.05 (s, 2H): MS (ES+) 585.

Example 18

2-(S)-[(3-Benzyl-6,7-dihydro-5H-pyrrolo[2,1-c][1,2,4]triazole-5-(S)-carbonyl)-amino]-3-(2',6'-dimethoxy-biphenyl-4-yl)-propionic acid (Cpd 13)

3-Benzyl-6,7-dihydro-5H-pyrrolo[2,1-c][1,2,4]triazole-5-carboxylic acid methyl ester was prepared using the method provided in Procedure 3, substituting (S)-methyl 2-pyrrolidone-5-carboxylate (3.0 g) for Compound 4a and substituting phenylacetic hydrazide (2.17 g) for benzoic hydrazide.

Using the method described in Example 10, substituting 4-Bromo-L-phenylalanine (5.0 g) for 4-Borono-L-phenylalanine, and substituting 2,6-dimethoxyphenylboronic acid (4.1 g) for 4-Bromo-5-methoxy-2-methyl-2H-pyridazin-3-one in Procedure 8, 3-Benzyl-6,7-dihydro-5H-pyrrolo[2,1-c][1,2,4]triazole-5-carboxylic acid methyl ester was converted to Compound 13. $^1$H NMR (300 MHz, CDCl$_3$) δ 7.09-7.32 (m, 10H), 6.67-6.72 (m, 2H), 4.70-4.77 (m, 2H), 3.66 (s, 2H), 3.61 (s, 6H), 4.81-4.86 (m, 1H), and 2.82-3.40 (m, 6H): MS (ES+) 527.

Example 19

2-(S)-[(3-Aminomethyl-6,7-dihydro-5H-pyrrolo[2,1-c][1,2,4]triazole-5-(S)-carbonyl)-amino]-3-[4-(2,6-dichloro-benzoylamino)-phenyl]-propionic acid (Cpd 14)

Compound 11 was dissolved in EtOAc (1.0 mL). 1N HCl (1.0 mL) and 10% Pd/C (5.0 mg) were added and the mixture was hydrogenated at 50 psi H$_2$ for 24 h. The mixture was filtered through CELITE® and concentrated in vacuo. Compound 14 was isolated. $^1$H NMR (300 MHz, CDCl$_3$) δ 7.33-7.61 (m, 7 H), 4.78-4.89 (m, 2H), 3.32 (s, 2H), and 2.98-3.30 (m, 6H): MS (ES+) 518.

Example 20

3-(2',6'-Dimethoxy-biphenyl-4-yl)-2-(S)-[(3-thiophen-3-ylmethyl-6,7-dihydro-5H-pyrrolo[2,1-c][1,2,4]triazole-5-(S)-carbonyl)-amino]-propionic acid (Cpd 15)

3-Thiophen-3-ylmethyl-6,7-dihydro-5H-pyrrolo[2,1-c][1,2,4]triazole-5-carboxylic acid methyl ester was prepared using the method provided in Procedure 3, substituting (S)-methyl 2-pyrrolidone-5-carboxylate (2.0 g) for Compound 4a and substituting thiophen-3-yl-acetic acid hydrazide (2.29 g) for benzoic hydrazide.

Using the method described in Example 10, substituting 4-Bromo-L-phenylalanine (5.0 g) for 4-Borono-L-phenylalanine, and substituting 2,6-dimethoxyphenylboronic acid (4.1 g) for 4-Bromo-5-methoxy-2-methyl-2H-pyridazin-3-one in Procedure 8, 3-Thiophen-3-ylmethyl-6,7-dihydro-5H-pyrrolo[2,1-c][1,2,4]triazole-5-carboxylic acid methyl ester was converted to the title compound 15. $^1$H NMR (300 MHz, CDCl$_3$) δ 7.19-7.33 (m, 6H), 6.70-6.76 (m, 2H), 6.68 (d, J=8.4 Hz, 2H), 4.64-4.69 (m, 1H), 4.31-4.36 (m, 1H), 3.94-4.00 (m, 1H), 3.65-3.71 (m, 1H), 3.61 (s, 6H), 3.37 (s, 2H), and 2.74-3.01 (m, 4H): MS (ES+) 533.

Example 21

3-(2',6'-Dimethoxy-biphenyl-4-yl)-2-{[3-(1H-indol-3-ylmethyl)-6,7-dihydro-5H-pyrrolo[2,1-c][1,2,4]triazole-5-carbonyl]-amino}-propionic acid (Cpd 16)

Using the method described in Example 20, substituting (1H-Indol-3-yl)-acetic acid hydrazide (2.79 g) for thiophen-3-yl-acetic acid hydrazide in Procedure 3, the title compound 16 was prepared. $^1$H NMR (300 MHz, CDCl$_3$) δ 7.11-7.35 (m, 8H), 7.02-7.07 (m, 1H), 6.69-6.93 (m, 2H), 4.71-4.84 (m, 1H), 4.15-4.20 (m, 1H), 4.00-4.03 (m, 1H), 3.84-3.94 (m, 1H), 3.61 (s, 6H), 3.36 (s, 2H), 2.90-2.98 (m, 1H), 2.54-2.69 (m, 2H), and 2.08-2.19 (m, 1H): MS (ES+) 566.

Compounds 1 to 17 of Formula (Ia) were prepared by the methods described in the schemes and specific examples described herein.

TABLE 1

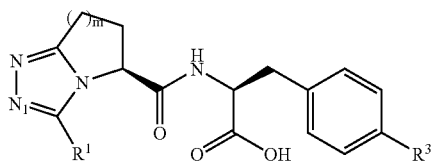

Formula (Ia)

| Cpd | R¹ | m | R³ |
|---|---|---|---|
| 1 | Phenyl | 2 | —O(C=O)NMe₂ |
| 2 | —CH₂Ph | 2 | —O(C=O)NMe₂ |
| 3 | —CH₂Ph | 1 | —O(C=O)NMe₂ |
| 4 | —CH₂Ph | 1 | —NH(C=O)2,6-dichlorophenyl |
| 5 | —CH₂Ph | 1 | —NH(C=O)naphthalen-1-yl |
| 6 | —CH₂Ph | 1 | —NH(C=O)naphthalen-2-yl |
| 7 | —CH₂Ph | 1 | —NH(C=O)(2-ethoxy-naphthalen-1-yl) |
| 8 | —CH₂Ph | 1 | —NH(C=O)fluoren-9-on-4-yl |
| 9 | —CH₂Ph | 1 | —NH(=O)3,5-dichloro pyridin-4yl |
| 10 | n-Propyl | 1 | —NH(C=O)2,6-dichlorophenyl |
| 11 | —CH₂NH(C=O)Obenzyl | 1 | —NH(C=O)2,6-dichlorophenyl |
| 12 | —CH₂-thiophen-3-yl | 1 | —NH(C=O)2,6-dichlorophenyl |
| 13 | —CH₂Ph | 1 | 2,6-methoxyphenyl |
| 14 | —CH₂NH₂ | 1 | —NH(C=O)2,6-dichlorophenyl |
| 15 | —CH₂-thiophen-3-yl | 1 | 2,6-methoxyphenyl |
| 16 | —CH₂-indol-3-yl | 1 | 2,6-methoxyphenyl |
| 17 | —CH₂Ph | 1 | 5-methoxy-2-methyl-2H-pyridazin-3-on-4-yl |

Compounds 18 to 21 of Formula (Ib) were prepared by the methods described in the schemes and specific examples described herein.

TABLE 2

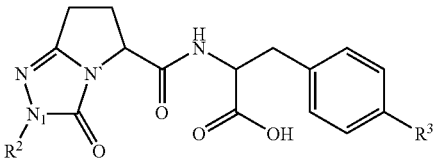

Formula (Ib)

| Cpd | R² | R³ |
|---|---|---|
| 18 | H | —NH(C=O)2,6-dichlorophenyl |
| 19 | —CH₂Ph | —NH(C=O)2,6-dichlorophenyl |
| 20 | H | —NHC(=O)3,5-dichloropyridin-4yl |
| 21 | —CH₂Ph | —NHC(=O)3,5-dichloropyridin-4yl |

Biological Examples

As demonstrated by the biological studies described hereinafter, and shown in Table 3, compounds of the present invention are α4β1 and α4β7 integrin receptor agonists useful in treating integrin mediated disorders including, but not limited to, inflammatory, autoimmune and cell-proliferative disorders.

Example 1

Ramos Cell Adhesion Assay ($\alpha_4\beta_1$ Mediated Adhesion/VCAM-1)

Immulon 96 well plates (Dynex) were coated with 100 μL recombinant hVCAM-1 at 4.0 μg/mL in 0.05 M NaCO₃ buffer pH 9.0 overnight at 4° C. (R&D Systems). Plates were washed 3 times in PBS with 1% BSA and blocked for 1 h @ room temperature in this buffer. PBS was removed and compounds to be tested (50 μL) were added at 2× concentration. Ramos cells, (50 μL at 2×10⁶/mL) labeled with 5 μM Calcein AM (Molecular Probes) for 1 h at 37° C., were added to each well and allowed to adhere for 1 h at room temperature. Plates were washed 3× in PBS+1% BSA and cells were lysed for 15 minutes in 100 μL of 1 M Tris pH 8.0 with 1% SDS. The plate was read at 485 nm excitation and 530 nm emission. The resultant data is shown in Table 1.

Example 2

$\alpha_4\beta_7$-K562 Cell Adhesion Assay ($\alpha_4\beta_7$ Mediated Adhesion/MAdCAM-1)

M2 anti-FLAG antibody coated 96-well plates (Sigma) were coated for 1 hour at 4° C. with 2-8 μl/well recombinant FLAG-hMAdCAM-1 contained in 100 μL of Dulbecco's PBS, pH 7.4, with 1% BSA and 1 mM Mn²⁺ (PBS-BSA-Mn). Plates were washed once with PBS-BSA-Mn. Buffer was removed and compounds to be tested (50 μL) were added at 2 times concentration. Stably transfected K562 cells expressing human α₄β₇ integrin, (50 μL at 2×10⁶/mL) that had been labeled with 100 μg/mL carboxymethyl fluorescein diacetate succinimidyl ester (CFDA-SE; Molecular Probes) for 15 min at 37° C. were added to each well and allowed to adhere for 1 h at room temperature. Plates were washed 4 times in PBS-BSA-Mn and then cells were lysed for 2 minutes by addition of 100 μL of PBS without Ca, Mg supplemented with 0.1 M NaOH. The plate was read on a 96-well fluorescent plate reader at 485 nm excitation and 530 nm emission. The resultant data is shown in Table 3.

TABLE 3

| Cpd | α4β1 IC50 (μM) | α4β7, Madcam IC50 (μM) |
|---|---|---|
| 1 | 3.30 | 1.22 |
| 2 | 5.09 | 1.66 |
| 3 | 4.15 | >5 |
| 4 | 0.62 | 0.29 |
| 5 | >5 | >5 |
| 6 | >5 | >5 |
| 7 | >5 | >5 |
| 8 | 1.56 | 0.35 |
| 9 | 0.08 | 0.02 |
| 10 | 1.04 | 0.08 |
| 11 | >5 | 0.55 |
| 12 | 0.38 | 0.12 |
| 13 | 1.19 | 0.32 |
| 14 | >5 | 0.00 |
| 15 | 0.71 | 0.09 |
| 16 | >5 | 0.04 |
| 17 | 0.64 | 0.40 |
| 18 | 0.85 | 0.09 |

TABLE 3-continued

| Cpd | α4β1 IC50 (μM) | α4β7, Madcam IC50 (μM) |
|---|---|---|
| 19 | >5 | 0.20 |
| 20 | 0.45 | 0.05 |
| 21 | >5 | 0.78 |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

All publications disclosed in the above specification are hereby incorporated by reference in full.

What is claimed is:

1. A compound of Formula (I):

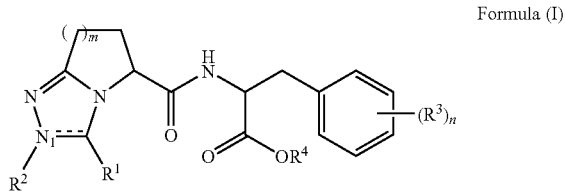

Formula (I)

wherein:

$R^1$ is a substituent selected from the group consisting of hydrogen, $C_{1-4}$alkyl, aryl($C_{1-8}$)alkyl, heteroaryl($C_{1-8}$)alkyl, aryl, amino($C_{1-4}$)alkyl, ($C_{1-4}$)alkylamino($C_{1-4}$)alkyl, di($C_{1-4}$)alkylamino($C_{1-4}$)alkyl, aryl($C_{1-4}$)alkoxycarbonylamino($C_{1-4}$)alkyl, heteroaryl($C_{1-4}$alkoxycarbonylamino($C_{1-4}$)alkyl, $C_{1-4}$alkoxycarbonylamino($C_{1-4}$)alkyl, aryloxycarbonylamino($C_{1-4}$)alkyl, and oxo;

wherein the $C_{1-4}$alkyl substituents of di($C_{1-4}$)alkylamino($C_{1-4}$)alkyl are optionally taken together with the nitrogen atom to which they are both attached to form a 5 to 8 membered monocyclic ring;

provided that when $R_1$ is a substituent other than oxo, a double bond exists between $N_1$ and the carbon bearing $R^1$; alternatively, when $R^1$ is oxo, then $R^2$ is present;

$R^2$ is selected from the group consisting of hydrogen, $C_{1-4}$alkyl, aryl($C_{1-4}$)alkyl, and heteroaryl($C_{1-4}$)alkyl;

m is an integer of 1 or 2;

$R^3$ is a substituent independently selected from the group consisting of $C_{1-8}$alkoxy, heterocyclyl, aryl, heteroaryl, benzo-fused heterocyclyl, —C(=O)NR$^A$R$^B$, —NR$^A$C(=O)aryl, —NR$^A$C(=O)heteroaryl, —NR$^A$C(=O)heterocyclyl, —NR$^A$C(=O)C$_{1-8}$alkyl, —NR$^A$C(=O)C$_{2-8}$alkenyl, —NR$^A$C(=O)C$_{2-8}$alkynyl, —NR$^A$(C=O)C$_{1-8}$alkoxy, —NR$^A$(C=O)C$_{1-8}$alkoxyaryl, —NR$^A$(C=O)C$_{1-8}$alkoxyheteroaryl, —NR$^A$SO$_2$-aryl, —NR$^A$SO$_2$-heteroaryl, —NR$^A$(C=O)C$_{1-8}$)alkyl, —NR$^A$C(=O)NR$^A$R$^B$, —NR$^A$C(=O)NR$^A$aryl, —NR$^A$C(=O)NR$^A$heteroaryl, —OC(=O)NR$^A$R$^B$, and halogen;

wherein heterocyclyl and the heterocyclyl-containing substituents of $R^3$, aryl and the aryl-containing substituents of $R^3$, benzo-fused heterocyclyl, and heteroaryl and the heteroaryl-containing substituents of $R^3$ are optionally substituted with one to five substituents independently selected from the group consisting of halogen, $C_{1-8}$alkyl, $C_{2-8}$alkenyl, $C_{2-8}$alkynyl, $C_{1-8}$alkoxy, $C_{1-8}$alkylcarbonyl, $C_{1-8}$alkoxycarbonyl, carboxyl, aryl, heteroaryl, aryloxy, heteroaryloxy, cycloalkyloxy, heterocyclyloxy, benzyloxycarbonyl, arylcarbonyl, heteroarylcarbonyl, arylsulfonyl, amino, $C_{1-8}$alkylamino, $C_{1-8}$alkylamino, —CF$_3$ and —OCF$_3$; provided that no more than one substituent is selected from the group consisting of aryl, heteroaryl, aryloxy, heteroaryloxy, cycloalkyloxy, heterocyclyloxy, benzyloxycarbonyl, arylcarbonyl, heteroarylcarbonyl, and arylsulfonyl;

and, wherein heterocyclyl of the heterocyclyl-containing substituents of $R^3$ is optionally further substituted with one to three oxo substituents;

$R^A$ is independently selected from the group consisting of hydrogen and $C_{1-8}$alkyl;

$R^B$ is independently selected from the group consisting of hydrogen, $C_{1-8}$alkyl, $C_{2-8}$alkenyl, $C_{2-8}$alkynyl, and (halo)$_{1-3}$($C_{1-8}$)alkyl; wherein $C_{1-8}$alkyl, $C_{2-8}$alkenyl and $C_{2-8}$alkynyl are optionally substituted with one to three substituents independently selected from the group consisting of heterocyclyl, aryl, and heteroaryl wherein the heterocyclyl, aryl, and heteroaryl substituents are optionally substituted with benzyloxycarbonyl, arylcarbonyl, or heteroarylcarbonyl, and optionally substituted with one to three substituents independently selected from the group consisting of halogen, $C_{1-8}$alkyl, $C_{2-8}$alkenyl, $C_{2-8}$alkynyl, $C_{1-8}$alkoxy, $C_{1-8}$alkylcarbonyl, $C_{1-8}$alkoxycarbonyl, carboxyl, —CF$_3$ and —OCF$_3$;

n is an integer from 0 to 3;

$R^4$ is a substituent independently selected from the group consisting of hydrogen and $C_{1-8}$alkyl;

and pharmaceutically acceptable enantiomers, diastereomers, racemates, and salts thereof.

2. A compound according to claim 1 wherein $R^1$ is independently selected from the group consisting of hydrogen, $C_{1-4}$alkyl, aryl($C_{1-8}$)alkyl, heteroaryl($C_{1-8}$)alkyl, aryl, and oxo; provided that when $R^1$ is a substituent other than oxo, a double bond exists between $N_1$ and the carbon bearing $R^1$; alternatively, when $R^1$ is oxo, then $R^2$ is present.

3. A compound according to claim 2 wherein $R^1$ is independently selected from the group consisting of $C_{1-4}$alkyl, aryl($C_{1-4}$alkyl, heteroaryl($C_{1-4}$alkyl, aryl, and oxo.

4. A compound according to claim 3 wherein aryl is phenyl.

5. A compound according to claim 4 wherein $C_{1-4}$alkyl is propyl, aryl($C_{1-4}$)alkyl is benzyl, heteroaryl($C_{1-4}$)alkyl is selected from the group consisting of thiophen-3-ylmethyl and indol-3-ylmethyl.

6. A compound according to claim 1 wherein $R^2$ is independently selected from the group consisting of hydrogen, $C_{1-4}$alkyl, and aryl($C^{1-4}$)alkyl.

7. A compound according to claim 6 wherein $R^2$ is independently selected from the group consisting of hydrogen and aryl($C_{1-4}$)alkyl.

8. A compound according to claim 7 wherein aryl($C_{1-4}$alkyl is benzyl.

9. A compound according to claim 1 wherein m is 1.

10. A compound according to claim 1 wherein $R^3$ is a substituent independently selected from the group consisting of $C_{1-6}$alkoxy, —C(=O)NR$^A$R$^B$, —NR$^A$C(=O)aryl, NR$^A$C(=O)heteroaryl, NR$^A$C(=O)heterocyclyl, —NR$^A$C(=O)C$_{1-8}$alkyl, —NR$^A$SO$_2$-aryl, —NR$^A$SO$_2$heteroaryl, —NR$^A$SO$_2$(C$_{1-8}$)alkyl, —NR$^A$C(=O)NR$^A$R$^B$, NR$^A$C(=O)NR$^A$aryl, NR$^A$C(=O)NR$^A$heteroaryl, —OC(=O)NR$^A$R$^B$, and halogen; wherein the heterocyclyl portion of NR$^A$C(=O)heterocyclyl, the aryl portion of the aryl-containing substituents of $R^3$, and the heteroaryl portion of the heteroaryl-containing substituents of R³ are optionally substituted with one to three substituents independently selected from the group consisting of halogen, $C_{1-4}$alkyl, $C_{1-4}$alkoxy, $C_{1-4}$alkylcarbonyl, $C_{1-4}$alkoxycarbonyl, amino, $C_{1-8}$alkylamino, $C_{1-8}$alkylamino, —$CF_3$ and —$OCF_3$; and, wherein heterocyclyl of —$NR^AC(=O)$heterocyclyl is optionally further substituted with one to two oxo substituents.

11. A compound according to claim 10 wherein R³ is a substituent independently selected from the group consisting of $C_{1-3}$alkoxy, —$C(=O)NR^AR^B$, —$NR^AC(=O)$aryl, —$NR^AC(=O)$heteroaryl, —$NR^AC(=O)C_{1-4}$alkyl, —$NR^ASO_2$aryl, —$NR^ASO_2$-heteroaryl, —$NR^ASO_2(C_{1-4})$alkyl, —$OC(=O)NR^AR^B$, and halogen; wherein the aryl portion of the aryl-containing substituents of R³, and the heteroaryl portion of the heteroaryl-containing substituents of R₃ are optionally substituted with one to three substituents independently selected from the group consisting of halogen, $C_{1-4}$alkyl, $C_{1-4}$alkoxy, and $C_{1-4}$alkoxycarbonyl.

12. A compound according to claim 11 wherein R³ is a substituent independently selected from the group consisting of $NR^AC(=O)$aryl, —$NR^AC(=O)$heteroaryl, —$NR^AC(=O)C_{1-4}$alkyl, and —$OC(=O)NR^A R^B$.

13. A compound according to claim 12 wherein $NR^AC(=O)$aryl is selected from the group consisting of —$NR^AC(=O)$phenyl and —$NR^AC(=O)$naphthalenyl, —$NR^AC(=O)$heteroaryl is —$NR^AC(=O)$pyridin-4-yl, and —$OC(=O)NR^AR^B$ is —$OC(=O)NMe_2$.

14. A compound according to claim 13 wherein in the optional substituents, halogen is chloro, $C_{1-4}$alkyl methyl, $C_{1-4}$alkoxy is methoxy or ethoxy, and $C_{1-4}$alkoxycarbonyl is methoxy carbonyl.

15. A compound according to claim 12 wherein R³ is a substituent independently selected from the group consisting of $NR^AC(=O)$aryl and —$NR^AC(=O)$heteroaryl.

16. A compound according to claim 15 wherein $NR^AC(=O)$aryl is selected from the group consisting of —NHC(=O)2,6-dichloro-phenyl, —NHC(=O)2,6-dimethoxyphenyl, —NHC(=O)naphthalen-1-yl, NHC(=O)2-ethoxynaphthalen-1-yl, and —NHC(=O)naphthalen-2-yl, and $NR^AC(=O)$heteroaryl is —NHC(=O)3,5-dichloro-pyridin-4-yl.

17. A compound according to claim 16 wherein R³ is attached at the 4-position of the phenyl ring of Formula (I).

18. A compound according to claim 1 wherein $R^A$ is independently selected from the group consisting of hydrogen and methyl.

19. A compound according to claim 1 wherein $R^B$ is independently selected from the group consisting of hydrogen, $C_{1-6}$alkyl, and $(halo)_{1-3}(C_{1-6})$alkyl; wherein $C_{1-6}$alkyl is optionally substituted with one to three substituents independently selected from the group consisting of heterocyclyl, aryl, and heteroaryl; wherein the heterocyclyl, aryl, and heteroaryl substituents are optionally substituted with benzyloxycarbonyl, arylcarbonyl, heteroarylcarbonyl, and optionally further substituted with one to three substituents independently selected from the group consisting of halogen, $C_{1-8}$alkyl, $C_{1-8}$alkoxy, $C_{1-8}$alkylcarbonyl, $C_{1-8}$alkoxycarbonyl, carboxyl, —$CF_3$ and —$OCF_3$.

20. A compound according to claim 19 wherein $R^B$ is independently selected from the group consisting of hydrogen and $C_{1-6}$alkyl.

21. A compound according to claim 20 wherein $C_{1-6}$alkyl is $C_{1-4}$alkyl.

22. A compound according to claim 21 wherein $C_{1-4}$alkyl is optionally substituted with one to three substituents independently selected from the group consisting of heterocyclyl, aryl, and heteroaryl.

23. A compound according to claim 1 wherein n is an integer from 0 to 2.

24. A compound according to claim 23 wherein n is 1.

25. A compound according to claim 1 wherein R⁴ is a substituent independently selected from the group consisting of hydrogen and $C_{1-4}$alkyl.

26. A compound according to claim 25 wherein $C_{1-4}$alkyl is methyl.

27. A compound of Formula (Ia):

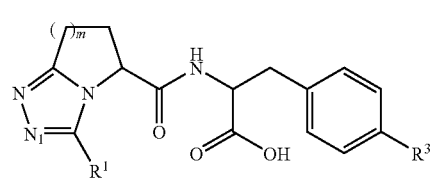

Formula (Ia)

selected from the group consisting of:

a compound of Formula (Ia) wherein R¹ is phenyl, m is 2, and R³ is —O(C=O)NMe₂;

a compound of Formula (Ia) wherein R¹ is —CH₂Ph, m is 2, and R³ is —O(C=O)NMe₂;

a compound of Formula (Ia) wherein R¹ is —CH₂Ph, m is 1, and R³ is —O(C=O)NMe₂;

a compound of Formula (Ia) wherein R¹ is —CH₂Ph, m is 1, and R³ is —NH(C=O)2,6—dichlorophenyl;

a compound of Formula (Ia) wherein R¹ is —CH₂Ph, m is 1, and R³ is —NH(C=O)naphthalen-1-yl;

a compound of Formula (Ia) wherein R¹ is —CH₂Ph, m is 1, and R³ is —NH(C=O)naphthalen-2-yl;

a compound of Formula (Ia) wherein R¹ is —CH₂Ph, m is 1, and R³ is —NH(C=O)(2-ethoxy)-naphthalen-1-yl;

a compound of Formula (Ia) wherein R¹ is —CH₂Ph, m is 1, and R³ is —NH(C=O)fluoren-9-on-4-yl;

a compound of Formula (Ia) wherein R¹ is —CH₂Ph, m is 1, and R³ is —NHC(=O)(3,5-dichloro)-pyridin-4-yl;

a compound of Formula (Ia) wherein R¹ is n-propyl, m is 1, and R³ is —NH(C=O)2,6-dichlorophenyl;

a compound of Formula (Ia) wherein R¹ is —CH₂NH(C=O)OCH₂Ph, m is 1, and R³ is —NH(C=O)2,6-dichlorophenyl;

a compound of Formula (Ia) wherein R¹ is —CH₂-thiophen-3-yl, m is 1, and R³ is —NH(C=O)2,6-dichlorophenyl;

a compound of Formula (Ia) wherein R¹ is —CH₂Ph, m is 1, and R³ is 2,6-dimethoxy-phenyl;

a compound of Formula (Ia) wherein R¹ is —CH₂NH₂, m is 1, and R³ is —NH(C=O)2,6-dichlorophenyl;

a compound of Formula (Ia) wherein R¹ is —CH₂-thiophen-3-yl, m is 1, and R³ is 2,6-dimethoxy-phenyl;

a compound of Formula (Ia) wherein R¹ is —CH₂-indol-3-yl, m is 1, and R₃ is 2,6-dimethoxy-phenyl; and a compound of Formula (Ia) wherein R¹ is —CH₂Ph, m is 1, and R³ is 5-methoxy-2-methyl-2H-pyridazin-3-on-4-yl;

and pharmaceutically acceptable enantiomers, diastereomers, racemates, and salts thereof.

28. A compound of Formula (Ib):

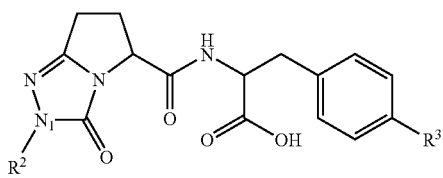

Formula (Ib)

selected from the group consisting of
a compound of Formula (Ib) wherein $R^2$ is H and $R^3$ is —NH(C=O)2,6-dichloro-phenyl;
a compound of Formula (Ib) wherein $R^2$ is —CH$_2$Ph and $R^3$ is —NH(C=O)2,6-dichloro-phenyl;
a compound of Formula (Ib) wherein $R^2$ is H and $R^3$ is —NHC(=O)3,5-dichloro-pyridin-4-yl; and
a compound of Formula (Ib) wherein $R^2$ is —CH$_2$Ph and $R^3$ is —NHC(=O)3,5-dichloro-pyridin-4-yl;
and pharmaceutically acceptable enantiomers, diastereomers, racemates, and salts thereof.

29. A compound of claim 1 wherein the compound is an effective antagonist of an integrin receptor.

30. A compound of claim 29 wherein the compound is a selective antagonist of an α4 integrin receptor.

31. A compound of claim 30 wherein the α4 integrin receptor is selected from the group consisting of the α4 β1 and α4 β7 integrin receptors.

32. A compound of claim 29 wherein the compound is an antagonist of at least two α4 integrin receptors.

33. A compound of claim 32 wherein the two α4 integrin receptors are selected from the group consisting of the α4 β1 and α4 β7 integrin receptors.

34. A compound of claim 1 wherein the compound is an effective agent for the treatment of an integrin mediated disorder is selected from the group consisting of asthma, bronchoconstriction, restenosis, atherosclerosis, psoriasis, rheumatoid arthritis, inflammatory bowel disease, irritable bowel disease, irritable bowel syndrome, transplant rejection and multiple sclerosis.

35. A compound of claim 34 wherein the integrin mediated disorder is selected from the group consisting of asthma, bronchoconstriction, restenosis, atherosclerosis, irritable bowel syndrome, and multiple sclerosis.

36. A pharmaceutical composition comprising a compound of claim 1 and a pharmaceutically acceptable carrier.

* * * * *

UNITED STATES PATENT AND TRADEMARK OFFICE
CERTIFICATE OF CORRECTION

PATENT NO. : 7,618,983 B2
APPLICATION NO. : 11/269369
DATED : November 17, 2009
INVENTOR(S) : Lawson et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 808 days.

Signed and Sealed this

Twelfth Day of October, 2010

David J. Kappos
*Director of the United States Patent and Trademark Office*